(12) United States Patent
Shinde et al.

(10) Patent No.: US 11,124,528 B2
(45) Date of Patent: Sep. 21, 2021

(54) PROCESS FOR PREPARING OPTICALLY ACTIVE 2,3-DIHYDROTHIAZOLO [3,2-A]PYRIMIDIN-4-IUM COMPOUNDS

(71) Applicant: BASF SE, Ludwigshafen am Rhein (DE)

(72) Inventors: Harish Shinde, Navi Mumbai (IN); Christopher Koradin, Ludwigshafen (DE); Joachim Dickhaut, Ludwigshafen (DE); Roland Goetz, Ludwigshafen (DE); Michael Rack, Ludwigshafen (DE); Eric George Klauber, Huntsville, AL (US); Sukunath Narayanan, Ludwigshafen (DE); Dhanyakumar Raut, Navi Mumbai (IN)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 16/608,290

(22) PCT Filed: Apr. 25, 2018

(86) PCT No.: PCT/EP2018/060555
§ 371 (c)(1),
(2) Date: Oct. 25, 2019

(87) PCT Pub. No.: WO2018/197541
PCT Pub. Date: Nov. 1, 2018

(65) Prior Publication Data
US 2020/0055872 A1    Feb. 20, 2020

(30) Foreign Application Priority Data

Apr. 27, 2017    (EP) .................................... 17168354

(51) Int. Cl.
| | | |
|---|---|---|
| *C07D 513/04* | (2006.01) | |
| *C07D 417/04* | (2006.01) | |
| *C07D 277/32* | (2006.01) | |

(52) U.S. Cl.
CPC ......... *C07D 513/04* (2013.01); *C07D 277/32* (2013.01); *C07D 417/04* (2013.01)

(58) Field of Classification Search
CPC ... C07D 513/04; C07D 417/04; C07D 277/32
See application file for complete search history.

(56) References Cited

FOREIGN PATENT DOCUMENTS

WO    WO 2018202654    * 11/2018

* cited by examiner

*Primary Examiner* — Bruck Kifle
(74) *Attorney, Agent, or Firm* — Marshall, Gerstein & Borun LLP

(57) ABSTRACT

The present invention relates to a process for preparing optically active compounds of formula X and intermediates thereof, wherein the variables of compound of formula X are as defined in the claims or the description.

19 Claims, No Drawings

PROCESS FOR PREPARING OPTICALLY ACTIVE 2,3-DIHYDROTHIAZOLO [3,2-A]PYRIMIDIN-4-IUM COMPOUNDS

This application is a National Stage application of International Application No. PCT/EP2018/060555, filed Apr. 25, 2018. This application also claims priority under 35 U.S.C. § 119 to European Patent Application No. 17168354.3, filed Apr. 27, 2017.

The present invention relates to a process for preparing an optically active pyrimidinium compounds of formula X according to the following reaction sequence:

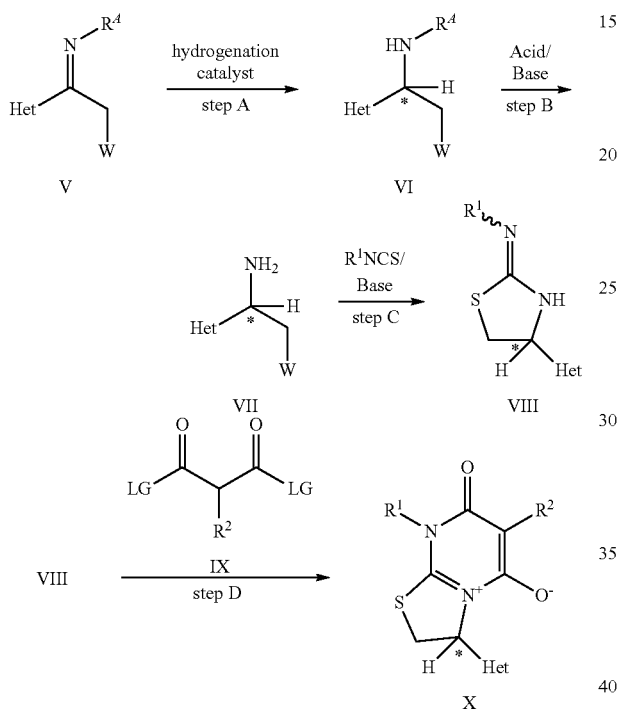

The present invention relates to a process for preparing an optically active pyrimidinium compound of formula X. The pyrimidinium compounds of formula X have insecticidal properties which is known from WO2014/167084. However, the process of preparing the optically enriched pyrimidinium compound of formula X is not described in the prior art. The present method to prepare optically active pyrimidinium compounds is based on an asymmetric transfer hydrogenation of acyclic imine derivative of formula V containing leaving groups, such as halogen, at α-carbon atom with respect to the imine functionality. Often hydrogenation of α-halo imines, such as α-halo imines of formula V, wherein W represents halogen, results into mixture of corresponding protodehalogenated compound (where W is hydrogen in formula VI) and forms aziridine derivative via displacement of α-halogen atom by amine nitrogen, in addition to the desired α-halo amines, such as compounds of formula VI. Further, it is known from the Literature that enantiomers can display different spectrum of pesticidal or insecticidal activities. It is also possible that while one specific enantiomer shows insecticidal activity, its counterpart may be completely inactive on insects. Thus, it has become a stringent requirement of any approval administration to use chiral compounds with pesticidal or insecticidal activity only in its respective active enantiomeric form.

Thus, there is a need for a process to prepare the optically active compound of formula X with more than 90% enantiomeric excess and with a high yield.

This object is achieved by the processes described in detail hereinafter.

A first aspect of the present invention relates to a process for preparing an optically active pyrimidinium compound of formula X,

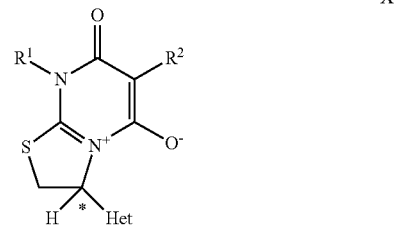

wherein

C* is an asymmetric carbon atom of S or R-configuration;

$R^1$ is $C_1$-$C_4$-alkyl, $C_3$-$C_6$-cycloalkyl, $C_2$-$C_4$-alkenyl or —$CH_2$-phenyl, which groups are unsubstituted or substituted with halogen or $C_1$-$C_4$-alkyl;

$R^2$ is a 5- or 6-membered saturated, partially unsaturated or aromatic carbo- or heterocyclic ring, wherein the ring is unsubstituted or substituted with $R^{2a}$;

Het is selected from D-1, D-2, and D-3:

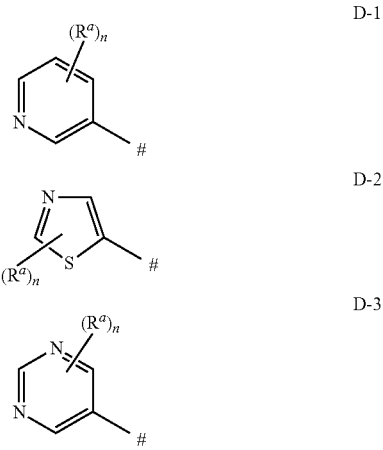

wherein $R^a$ is each independently halogen, $C_1$-$C_4$-haloalkyl, $C_1$-$C_4$-alkoxy, $C_1$-$C_4$-alkylthio, or phenyl;

n is 0, 1, or 2, and # denotes the bond in formula X;

$R^{2a}$ is halogen, $C_1$-$C_6$-haloalkyl, $C_1$-$C_6$-haloalkoxy, $OR^c$, $C(\!=\!O)OR^c$, $C(\!=\!O)NR^bR^c$, phenyl, or pyridyl, which groups are unsubstituted or substituted with halogen, $C_1$-$C_6$-haloalkyl, or $C_1$-$C_6$-haloalkoxy;

$R^b$ is hydrogen, $C_1$-$C_6$-alkyl, $C_1$-$C_6$-haloalkyl, $C_1$-$C_6$-alkoxy, or $C_1$-$C_6$-haloalkoxy;

$R^c$ is hydrogen, $C_1$-$C_4$-alkyl, $C_1$-$C_4$-haloalkyl, or $C_1$-$C_6$ cycloalkyl;

wherein two geminally bound groups $R^cR^b$ together with the atom to which they are bound may form a 3- to 7-membered saturated, partially unsaturated or aromatic heterocyclic ring;

comprising at least the steps of, (A) hydrogenation of a compound of formula V,

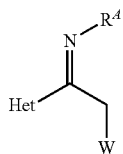

V wherein $R^A$ is $S(=O)_oR^x$, $P(=O)(R^x)_2$, $C_1$-$C_4$-alkoxy, or —$CH_2$-phenyl, wherein phenyl is unsubstituted or substituted with halogen, methoxy, or nitro;

wherein $R^x$ is $C_1$-$C_6$ alkyl or aryl which is unsubstituted or substituted with halogen; and o is 1 or 2;

W is halogen, hydroxy, O-p-toluenesulphonyl, O-methanesulphonyl, or O-trifluoromethanesulphonyl;

Het is as defined in the compound of formula X;

in the presence of a hydrogenation catalyst $MXLn(\eta\text{-arene})_m$, wherein M is a transition metal from group VIII to group XII of the periodic table;

X is an anion;

m is 0 or 1;

Ln is Ln1 or Ln2, wherein

Ln1 is a chiral ligand of the formula Ln1

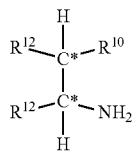

Ln1 wherein

C* is an asymmetric carbon atom of S or R-configuration;

$R^{10}$ is OH or NH—$SO_2$—$R^{11}$; wherein $R^{11}$ is aryl unsubstituted or substituted with halogen, $C_1$-$C_{10}$-alkyl, $C_1$-$C_4$-alkoxy, $C_3$-$C_6$-cycloalkyl, $SO_3H$, or $SO_3Na$;

or $C_1$-$C_{10}$-perfluoroalkyl, or $R^{13}R^{14}N$ wherein $R^{13}$ and $R^{14}$ independently represent $C_1$-$C_{10}$-alkyl unsubstituted or substituted with $C_6$-$C_{10}$-aryl, or $R^{13}$ and $R^{14}$ each independently represents a $C_6$-$C_{10}$-cycloalkyl;

$R^{12}$ independently represents $C_6$-$C_{10}$-aryl ring or $C_6$-$C_{10}$-cycloalkyl ring, wherein the ring is unsubstituted or substituted independently of each other with halogen, $C_1$-$C_{10}$-alkyl, $C_1$-$C_4$-alkoxy, $C_3$-$C_6$-cycloalkyl, $SO_3H$, or $SO_3Na$, or both $R^{12}$ are linked together to form a 3- to 6-membered carbocyclic ring or a 5- to 10-membered partially unsaturated carbocyclic ring;

Ln2 is a chiral phosphorous ligand;

and a hydrogen source selected from a) hydrogen, b) mixture of $N(R)_3$ wherein R is H or $C_1$-$C_6$-alkyl, and HCOOH, c) HCOONa or HCOOK, d) mixture of $C_1$-$C_8$-alcohol and t-BuOK, t-BuONa, or t-BuOLi, and e) combination of two or more from a) to d);

to obtain a compound of formula VI,

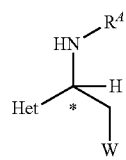

VI wherein C*, $R^A$, Het and W are as defined in the compound of formula V.

(B) hydrolyzing the compound of formula VI as defined herein, in the presence of an acid or a base, to obtain a compound of formula VII

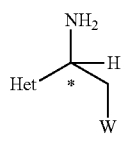

VII wherein C*, Het, and W are as defined in the compound of formula VI.

(C) reacting the compound of formula VII as defined herein, with $R^1NCS$, wherein $R^1$ is $C_1$-$C_4$-alkyl, $C_3$-$C_6$-cycloalkyl, $C_2$-$C_4$-alkenyl, or —$CH_2$-phenyl, which groups are unsubstituted or substituted with halogen or $C_1$-$C_4$-alkyl, in the presence of a base, to obtain a compound of formula VIII,

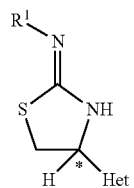

VIII wherein C*, Het and $R^1$ are as defined in the compound of formula VII;

(D) reacting the compound of formula VIII as defined herein, with a compound of formula IX,

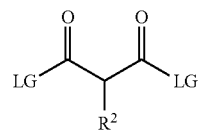

IX wherein,

LG is a leaving group selected from halogen, $OR^u$, or $SR^u$; wherein $R^u$ is $C_1$-$C_6$-alkyl, or aryl, which is unsubstituted or substituted with halogen;
$R^2$ is as defined in the compound of formula X;
to obtain the compound of formula X.

The process of preparing the compound of formula X, optionally further comprises a process of preparing the compound of formula V by at least the steps of
(E) reacting a compound of formula I,

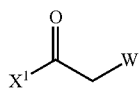

wherein W is as defined herein, and $X^1$ is halogen;
with $NH(R^Q)(R^P)$·HCl wherein $R^Q$ and $R^P$ independently are $C_1$-$C_6$-alkyl or $C_1$-$C_6$-alkoxy or $R^Q$ and $R^P$ are linked together to form a 5- to 7-membered carbocyclic or heterocyclic ring;
in the presence of a base,
to obtain the compound of formula II,

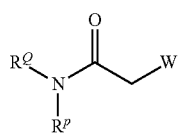

wherein $R^Q$, $R^P$ and W are as defined herein;
(F) reacting the Het as defined herein, with a compound of formula II as defined herein, in the presence of a $R^L MgX^1$ or $R^L Li$; wherein $R^L$ is $C_1$-$C_6$-alkyl; $X^1$ is halogen, and a metal halide wherein the metal is lithium, sodium, potassium, or magnesium;
to obtain the compound of formula III,

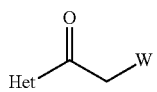

wherein Het and W are as defined herein;
(G) by reacting a compound of formula III as defined herein, with a compound of formula IV,

wherein $R^A$ is as defined in compound of formula V,
in the presence of Lewis acid, such as titanium(IV) alkoxide or copper(II)acetate, or in the presence of organic acids or inorganic acids,
to obtain the compound of formula V as defined herein.

The compound of formula III can also be prepared in analogy to the methods as described herein or methods known from WO 2014/167084 or other methods known in the literature.

Starting materials used in the process are commercially available or can be prepared by methods known in the literature.

Further aspect of the present invention relates to a process of preparing an optically active compound of formula X as defined herein, comprising one or more of the steps of (G), (F), (E), (D), (C), (B), and (A) as described herein, preferably in the sequence (G)→(F)→(E)→(A)→(B)→(C)→(D) as described herein.

Amine compounds, particularly the optically enriched amine compounds possessing leaving group at adjacent carbon atom to amine functionality, such as in formula VI, can be used as versatile intermediates in the preparation of several heterocyclic derivatives. Further, the optically enriched amines of formula VI can be used as versatile intermediates in preparation of fine chemicals, pharmaceuticals and agrochemicals. Furthermore, the compounds of formula VI are useful intermediates for the preparation of pesticides with amine derivative, or N containing heterocyclic moiety, for example compounds of formula VII, VIII or the compounds of formula X which are useful for combating invertebrate pests as reported in WO 2014/167084. However, a process of preparing the optically enriched compound of formula VI, possessing leaving group at adjacent carbon atom to amine functionality, is not known and processes known in the literature to prepare a compound analogous to the compound of formula VI are either disadvantageous in terms of the reaction conditions, the yields, and/or the work-up requirements or suffer from several limitations rendering them hardly suitable for industrial scale production Hence, there is a need to develop a process for preparing the optically enriched compound of formula VI, more specifically a process for preparing the optically enriched compound of formula VI with an enantiomeric excess, preferably >70%, more preferably >85%, most preferably >90%.

This object is achieved by providing the optically active compound of formula VI and a process for preparing the optically active compound of formula VI with an enantiomeric excess.

Further aspect of the present invention relates to a process of preparing a compound of formula VI as defined herein,

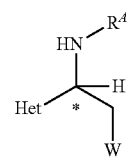

by hydrogenation of a compound of formula V as defined herein, as described in the step (A) herein.

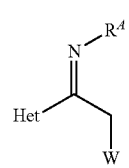

Further aspect of the present invention relates to a compound of formula V or salts, and N-oxides thereof.

Further aspect of the present invention relates to a compound of formula VI or salts and N-oxides thereof.

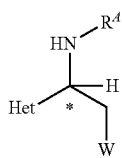

VI wherein C*, R^A, Het, and W are as defined herein.

Amine compounds, particularly the optically enriched amine compounds possessing leaving group at adjacent carbon atom to amine functionality, such as in formula VII, can be used as versatile intermediates in preparation of several heterocyclic derivatives. Further, the optically enriched amines of formula VII can be used as versatile intermediates in preparation of fine chemicals, pharmaceuticals and agrochemicals. Furthermore, the compounds of formula VII are useful intermediates for the preparation of pesticides with amine derivative, or N containing heterocyclic moiety, for example compounds of formula VIII or the compounds of formula X which are useful for combating invertebrate pests as reported in WO2014/167084. However, a process of preparing the optically enriched compound of formula VII, possessing leaving group at adjacent carbon atom to amine functionality, is not known and processes known in the literature to prepare a compound analogous to the compound of formula VII are either disadvantageous in terms of the reaction conditions, the yields, and/or the work-up requirements or suffer from several limitations rendering them hardly suitable for industrial scale production Hence there is a need to develop a process for preparing the optically active compound of formula VII, more specifically a process for preparing the optically active compound of formula VII with an enantiomeric excess, preferably >80%, more preferably >85%, most preferably >90%.

This object is achieved by providing the optically active compound of formula VII and a process for preparing the optically active compound of formula VII with an enantiomeric excess.

Further aspect of the present invention relates to a process of preparing a compound of formula VII as defined herein,

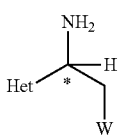

VII by hydrolyzing a compound of formula VI as defined herein,

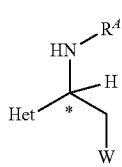

VI in the presence of an acid or base as described in the step (B) herein.

Further aspect of the present invention relates to a compound of formula VII or salts and N-oxides thereof.

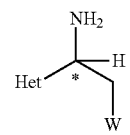

VII wherein C*, R¹, and W are as defined herein.

Further, the optically enriched thiazolidin-2-imine compounds of formula VIII can be used as versatile intermediate compounds for the preparation of compounds of formula X which are useful for combating invertebrate pests as reported in WO2014/167084. Further, the method for preparing optically enriched thiazolidin-2-imine compounds of formula VIII, as defined herein, is not reported in literature.

Hence there is a need to develop a process for preparing the optically enriched compound of formula VIII, more specifically a process for preparing the optically active compound of formula VIII with an enantiomeric excess, preferably >80%, more preferably >90%, most preferably >95%.

This object is achieved by providing the optically active compound of formula VIII and a process for preparing the optically active compound of formula VIII with an enantiomeric excess.

Further aspect of the present invention relates to a process of preparing the compound of formula VIII as defined herein,

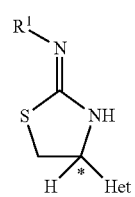

VIII by reacting a compound of formula VII as defined herein,

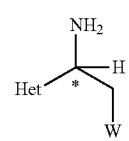

VII in the presence of a base, as described in the step (C) herein.

Further aspect of the present invention relates to a compound of formula VIII or salts and N-oxides thereof.

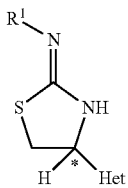

VIII wherein C*, Het and $R^1$ are as defined herein.

Further aspect of the present invention relates to a process of preparing the compound of formula X as defined herein, reacting the compound of formula VIII as defined herein, with a compound of formula IX as defined herein, as described in the step (D) herein.

The molecular structure of compound of formula X may exist in different isoelectronic formulae, each having the formal positive and negative charges on different atoms as shown below. The present invention extends to process of preparing all representative isoelectronic structures of compounds of formula X.

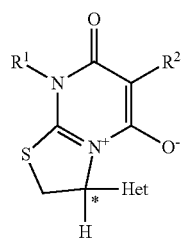

X

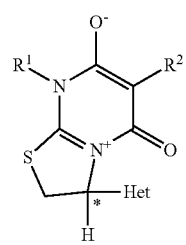

X

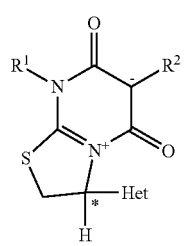

X

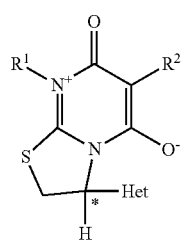

X

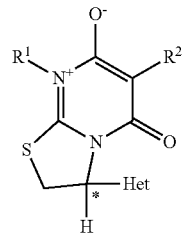

X

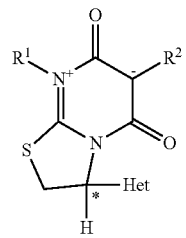

X

The "present invention", "invention" or "process of the present invention" refers to one or more of the steps (G), (F), (E), (D), (C), (B), and (A), preferably to one or more of the steps (D), (C), (B), and (A). The "compounds of the present invention" or "compounds according to the invention", i.e. the compounds of formulae VI, VII, or VIII as defined herein, comprise the compound(s) as well as salts, tautomers or N-oxides thereof, if the formation of these derivatives is possible.

The term "stereoisomer(s)" encompasses both optical isomers, such as enantiomers or diastereomers, the latter existing due to more than one center of chirality in the molecule, as well as geometrical isomers (cis/trans isomers). The present invention or the compounds of present invention relates to every possible stereoisomer of the compounds of the invention, i.e. to single enantiomers or diastereomers, as well as to the mixtures thereof.

The compounds according to the invention may be amorphous or may exist in one or more different crystalline states (polymorphs) which may have different macroscopic properties such as stability or show different biological properties such as activities. The present invention relates to amorphous and crystalline compounds according to the invention, mixtures of different crystalline states of the respective compounds according to the invention, as well as amorphous or crystalline salts thereof.

Salts of the compounds according to the invention can be formed in a customary manner, e.g. by reacting the compound with an acid of the anion in question if the compounds according to the invention have a basic functionality or by reacting acidic compounds according to the invention with a suitable base. Salts of the compounds according to the invention are preferably agriculturally and/or veterinary acceptable salts, preferably agriculturally acceptable salts.

The term "N-oxide" includes any compound of the present invention which has at least one tertiary nitrogen atom that is oxidized to an N-oxide moiety.

As used herein, the term "hydrogenation catalyst" covers homogeneous hydrogenation catalysts. It is known in the art that rhodium, ruthenium, iridium, platinum, palladium, iron or nickel form highly active catalysts. Preferred hydrogenation catalysts according to the invention are provided further below.

Anions of useful acid addition salts are primarily halides such as chloride, bromide, and fluoride; sulfonate, phosphate, nitrate, carbonate, hexafluorosilicate, hexafluorophosphate, benzoate, and the anions of $C_1$-$C_4$-alkanoic acids, preferably formate, acetate, propionate and butyrate. They can be formed by reacting the M or MLn with an acid of the corresponding anion, preferably of hydrochloric acid, hydrobromic acid, sulfuric acid, phosphoric acid or nitric acid.

The organic moieties or groups mentioned in the above definitions of the variables are—like the term halogen—collective terms for individual listings of the individual group members. The prefix $C_n$-$C_m$ indicates in each case the possible number of carbon atoms in the group.

"Halogen" will be taken to mean fluoro, chloro, bromo and iodo.

The term "partially or fully halogenated" will be taken to mean that 1 or more, e.g. 1, 2, 3, 4 or 5 or all of the hydrogen atoms of a given radical have been replaced by a halogen atom, in particular by fluorine or chlorine.

The term "$C_n$-$C_m$-alkyl" as used herein (and also in $C_n$-$C_m$-alkylamino, di-$C_n$-$C_m$-alkylamino, $C_n$-$C_m$-alkylaminocarbonyl, di-($C_n$-$C_m$-alkylamino)carbonyl, $C_n$-$C_m$-alkylthio, $C_n$-$C_m$-alkylsulfinyl and $C_n$-$C_m$-alkylsulfonyl) refers to a branched or unbranched saturated hydrocarbon group having n to m, e.g. 1 to 10 carbon atoms, preferably 1 to 6 carbon atoms, for example methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl and their isomers. $C_1$-$C_4$-alkyl means for example methyl, ethyl, propyl, 1-methylethyl, butyl, 1-methylpropyl, 2-methylpropyl or 1,1-dimethylethyl.

The term "$C_n$-$C_m$-haloalkyl" as used herein (and also in $C_n$-$C_m$-haloalkylsulfinyl and $C_n$-$C_m$-haloalkylsulfonyl) refers to a straight-chain or branched alkyl group having n to m carbon atoms, e.g. 1 to 10 in particular 1 to 6 carbon atoms (as mentioned above), where some or all of the hydrogen atoms in these groups may be replaced by halogen atoms as mentioned above, for example $C_1$-$C_4$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and the like. The term $C_1$-$C_{10}$-haloalkyl in particular comprises $C_1$-$C_2$-fluoroalkyl, which is synonym with methyl or ethyl, wherein 1, 2, 3, 4 or 5 hydrogen atoms are substituted with fluorine atoms, such as fluoromethyl, difluoromethyl, trifluoromethyl, 1-fluoroethyl, 2-fluoroethyl, 2,2-difluoroethyl, 2,2,2-trifluoroethyl and pentafluoromethyl.

Similarly, "$C_n$-$C_m$-alkoxy" and "$C_n$-$C_m$-alkylthio" (or $C_n$-$C_m$-alkylsulfenyl, respectively) refer to straight-chain or branched alkyl groups having n to m carbon atoms, e.g. 1 to 10, in particular 1 to 6 or 1 to 4 carbon atoms (as mentioned above) bonded through oxygen (or sulfur linkages, respectively) at any bond in the alkyl group. Examples include $C_1$-$C_4$-alkoxy such as methoxy, ethoxy, propoxy, isopropoxy, butoxy, sec-butoxy, isobutoxy and tert-butoxy, further $C_1$-$C_4$-alkylthio such as methylthio, ethylthio, propylthio, isopropylthio, and n-butylthio.

Accordingly, the terms "$C_n$-$C_m$-haloalkoxy" and "$C_n$-$C_m$-haloalkylthio" (or $C_n$-$C_m$-haloalkyl-sulfenyl, respectively) refer to straight-chain or branched alkyl groups having n to m carbon atoms, e.g. 1 to 10, in particular 1 to 6 or 1 to 4 carbon atoms (as mentioned above) bonded through oxygen or sulfur linkages, respectively, at any bond in the alkyl group, where some or all of the hydrogen atoms in these groups may be replaced by halogen atoms as mentioned above, for example $C_1$-$C_2$-haloalkoxy, such as chloromethoxy, bromomethoxy, dichloromethoxy, trichloromethoxy, fluoromethoxy, difluoromethoxy, trifluoromethoxy, chlorofluoromethoxy, di-chlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy and pentafluoroethoxy, further $C_1$-$C_2$-haloalkylthio, such as chloromethylthio, bromomethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-chloroethylthio, 1-bromoethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio and pentafluoroethylthio and the like. Similarly the terms $C_1$-$C_2$-fluoroalkoxy and $C_1$-$C_2$-fluoroalkylthio refer to $C_1$-$C_2$-fluoroalkyl which is bound to the remainder of the molecule via an oxygen atom or a sulfur atom, respectively.

The term "$C_2$-$C_m$-alkenyl" as used herein intends a branched or unbranched unsaturated hydrocarbon group having 2 to m, e.g. 2 to 10 or 2 to 6 carbon atoms and a double bond in any position, such as ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-di-methyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

The term "$C_2$-$C_m$-alkynyl" as used herein refers to a branched or unbranched unsaturated hydrocarbon group having 2 to m, e.g. 2 to 10 or 2 to 6 carbon atoms and containing at least one triple bond, such as ethynyl, propynyl, 1-butynyl, 2-butynyl, and the like.

The suffix "-carbonyl" in a group or "C(=O)" denotes in each case that the group is bound to the remainder of the molecule via a carbonyl C=O group. This is the case e.g. in alkylcarbonyl, haloalkylcarbonyl, aminocarbonyl, alkylaminocarbonyl, dialkylaminocarbonyl, alkoxycarbonyl, haloalkoxycarbonyl.

The term "aryl" as used herein refers to a mono-, bi- or tricyclic aromatic hydrocarbon radical such as phenyl or naphthyl, in particular phenyl (also referred as to $C_6H_5$ as substituent).

The term "ring system" denotes two or more directly connected rings.

The term "$C_3$-$C_m$-cycloalkyl" as used herein refers to a monocyclic ring of 3- to m-membered saturated cycloaliphatic radicals, e.g. cyclopropyl, cyclobutyl, cyclopentyl, cyclohexyl, cycloheptyl, cyclooctyl and cyclodecyl.

The term "5- to 10-membered partially unsaturated carbocyclic ring" as used herein refers to partially unsaturated monocyclic or bicyclic ring containing 5 to 10 carbon atoms, for example indane.

The term "3- to 7-membered carbocyclic ring" as used herein refers to cyclopropane, cyclobutane, cyclopentane, cyclohexane and cycloheptane rings.

The term "heterocyclic ring" refers "3-, 4-, 5-, 6- or 7-membered saturated, partially unsaturated or aromatic heterocyclic ring which may contain 1, 2, 3 or 4 heteroatoms" or "containing heteroatom groups", wherein those heteroatom(s) (group(s)) are selected from N (N-substituted groups), O and S (S-substituted groups) as used herein refers to monocyclic radicals, the monocyclic radicals being saturated, partially unsaturated or aromatic (completely unsaturated). The heterocyclic radical may be attached to the remainder of the molecule via a carbon ring member or via a nitrogen ring member.

Examples of 3-, 4-, 5-, 6- or 7-membered saturated heterocyclyl or heterocyclic rings include: oxiranyl, aziridinyl, azetidinyl, 2-tetrahydrofuranyl, 3-tetrahydrofuranyl, 2-tetrahydrothienyl, 3-tetrahydrothienyl, 2-pyrrolidinyl, 3-pyrrolidinyl, 3-pyrazolidinyl, 4-pyrazolidinyl, 5-pyrazolidinyl, 2-imidazolidinyl, 4-imidazolidinyl, 2-oxazolidinyl, 4-oxazolidinyl, 5-oxazolidinyl, 3-isoxazolidinyl, 4-isoxazolidinyl, 5-isoxazolidinyl, 2-thiazolidinyl, 4-thiazolidinyl, 5-thiazolidinyl, 3-isothiazolidinyl, 4-isothiazolidinyl, 5-isothiazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, -1,3,4-oxadiazolidin-2-yl, 1,3,4-thiadiazolidin-2-yl, 1,3,4-triazolidin-2-yl, 2-tetrahydropyranyl, 4-tetrahydropyranyl, 1,3-dioxan-5-yl, 1,4-dioxan-2-yl, 2-piperidinyl, 3-piperidinyl, 4-piperidinyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl, 2-morpholinyl, 3-morpholinyl, 2-thiomorpholinyl, 3-thiomorpholinyl, 1-oxothiomorpholin-2-yl, 1-oxothiomorpholin-3-yl, 1,1-dioxothiomorpholin-2-yl, 1,1-dioxothiomorpholin-3-yl, hexahydroazepin-1-, -2-, -3- or -4-yl, hexahydrooxepinyl, hexahydro-1,3-diazepinyl, hexahydro-1,4-diazepinyl, hexahydro-1,3-oxazepinyl, hexahydro-1,4-oxazepinyl, hexahydro-1,3-dioxepinyl, hexahydro-1,4-dioxepinyl and the like.

Examples of 3-, 4-, 5-, 6- or 7-membered partially unsaturated heterocyclyl or heterocyclic rings include: 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin 3 ylm, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3 dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-, 3-, 4-, 5- or 6-di- or tetrahydropyridinyl, 3-di- or tetrahydropyridazinyl, 4-di- or tetrahydropyridazinyl, 2-di- or tetrahydropyrimidinyl, 4-di- or tetrahydropyrimidinyl, 5-di- or tetrahydropyrimidinyl, di- or tetrahydropyrazinyl, 1,3,5-di- or tetrahydrotriazin-2-yl, 1,2,4-di- or tetrahydrotriazin-3-yl, 2,3,4,5-tetrahydro[1H] azepin-1-, -2-, -3-, -4-, -5-, -6- or -7-yl, 3,4,5,6-tetrahydro [2H]azepin-2-, -3-, -4-, -5-, -6- or -7-yl, 2,3,4,7 tetrahydro [1H]azepin-1-, -2-, -3-, -4-, -5-, -6- or -7-yl, 2,3,6,7 tetrahydro[1H]azepin-1-, -2-, -3-, -4-, -5-, -6- or -7-yl, tetrahydrooxepinyl, such as 2,3,4,5-tetrahydro[1H]oxepin-2-, -3-, -4-, -5-, -6- or -7-yl, 2,3,4,7 tetrahydro[1H]oxepin-2-, -3-, -4-, -5-, -6- or -7-yl, 2,3,6,7 tetrahydro[1H]oxepin-2-, -3-, -4-, -5-, -6- or -7-yl, tetrahydro-1,3-diazepinyl, tetrahydro-1,4-diazepinyl, tetrahydro-1,3-oxazepinyl, tetrahydro-1,4-oxazepinyl, tetrahydro-1,3-dioxepinyl and tetrahydro-1,4-dioxepinyl.

Examples of 5- or 6-membered aromatic heterocyclic (hetaryl) or heteroaromatic rings are: 2-furyl, 3-furyl, 2-thienyl, 3-thienyl, 2-pyrrolyl, 3-pyrrolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,3,4-triazol-2-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl and 2-pyrazinyl.

The term "chiral phosphorous ligand" covers all chiral phosphorous ligands known in the art for their use as ligand in metal catalyzed hydrogenation reaction, for example chiral phosphorous ligands known from "Rhodium-Catalyzed Asymmetric Hydrogenation, Yongxiang Chi, Wenjun Tang, and Xumu Zhang In: *Modern Rhodium-Catalyzed Organic Reactions*, eds. P. Andrew Evans, Wiley, page 1-31 (2005)" and "*Molecules* 2000, 5, 4-18".

The term "substituted" if not specified otherwise refers to substituted with 1, 2 or maximum possible number of substituents. If substituents as defined in compounds of formula I are more than one, then they are independently from each other are same or different if not mentioned otherwise.

Meaning of the terms that are not defined herein are generally known to a person skilled in the art or in the literature.

Preferred embodiments of the present invention are described below.

In one embodiment of the invention, $R^1$ is $C_1$-$C_4$-alkyl, $C_3$-$C_6$-cycloalkyl, or $C_2$-$C_4$-alkenyl.

In another embodiment, $R^1$ is $C_1$-$C_4$-alkyl.

In another embodiment, $R^1$ is methyl or ethyl.

In another embodiment, $R^1$ is methyl.

In one embodiment of the invention, $R^2$ is phenyl, pyridinyl or thiophenyl, which are unsubstituted or substituted with $R^{2a}$.

In another embodiment, $R^2$ is phenyl, which is unsubstituted or substituted with $R^{2a}$, wherein $R^{2a}$ is halogen, $C_1$-$C_6$-haloalkyl, $C_1$-$C_6$-haloalkoxy, $OR^c$, $C(=O)OR^c$, $C(=O)NR^bR^c$, phenyl, or pyridyl, which groups are unsubstituted or substituted with halogen, $C_1$-$C_6$-haloalkyl or $C_1$-$C_6$-haloalkoxy.

In another embodiment, $R^2$ is phenyl, which is unsubstituted or substituted with halogen, $C_1$-$C_4$-alkyl, or $C_1$-$C_3$-haloalkyl.

In another embodiment, $R^2$ is phenyl, which is unsubstituted or substituted with trifluoromethyl or halogen, preferably with chlorine;

In another embodiment, $R^2$ is phenyl, 3,5-dichlorophenyl, or 3-trifluoromethylphenyl.

In another embodiment, $R^2$ is phenyl.

In another embodiment, $R^2$ is 3,5-dichlorophenyl.

In another embodiment, $R^2$ is 3-trifluoromethylphenyl.

In an embodiment, $R^a$ is halogen, $C_1$-$C_6$-alkyl, $C_1$-$C_6$-haloalkyl, $C_1$-$C_6$-alkoxy, $C_1$-$C_6$-haloalkoxy, $C_3$-$C_6$-cycloalkyl, or CN.

In another embodiment, $R^a$ is halogen, $C_1$-$C_4$-haloalkyl, $C_1$-$C_4$-alkoxy, $C_1$-$C_4$-alkylthio, or phenyl.

In a preferred embodiment, $R^a$ is halogen or $C_1$-$C_6$-alkyl;

In a more preferred embodiment, $R^a$ is halogen or $C_1$-$C_6$-alkyl;

In a most preferred embodiment, $R^a$ is halogen, preferably Cl.

In another preferred embodiment, $R^a$ is phenyl.

In an embodiment, $R^A$ is $S(=O)R^x$.

In another embodiment, $R^A$ is $S(=O)_2R^x$.

In another embodiment, $R^A$ is $P(=O)(R^x)_2$.

In another embodiment, $R^A$ is $C_1$-$C_4$-alkoxy.

In another embodiment, $R^A$ is —$CH_2$-phenyl, wherein phenyl is unsubstituted or substituted with halogen, methoxy, or nitro.

In an embodiment, n is 0.

In another embodiment, n is 1.

In another embodiment, n is 2.

In one embodiment of the invention, Het is D-2;

In one embodiment of the invention, Het is selected from D-1, D-2 and D-3, wherein
$R^a$ is chloro,
n is 1

In another embodiment, Het is D-1a, D-2a and D-3a:

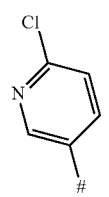

D-1a

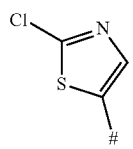

D-2a

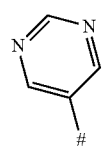

D-3a

In another embodiment, Het is D-1a.
In another embodiment, Het is D-2a.
In another embodiment, Het is D-3a.

In one embodiment of the invention, the compound of formula X is one of the following compounds X-1 to X-6:

| Compound No | $R^1$ | $R^2$ | Het |
|---|---|---|---|
| X-1 | $CH_3$ | Ph | D-1a |
| X-2 | $CH_3$ | Ph | D-2a |
| X-3 | $CH_3$ | Ph | D-3a |
| X-4 | $CH_3$ | 3-CF₃-C₆H₄ | D-2a |
| X-5 | $CH_3$ | 3,5-Cl₂-C₆H₃ | D-2a |
| X-6 | $CH_2CH_3$ | Ph | D-2a |

In one embodiment of the invention, the compound of formula X is the compound X-1.

In another embodiment of the invention, the compound of formula X is the compound X-2.

In another embodiment of the invention, the compound of formula X is the compound X-3.

In another embodiment of the invention, the compound of formula X is the compound X-4.

In another embodiment of the invention, the compound of formula X is the compound X-5.

In another embodiment of the invention, the compound of formula X is the compound X-6.

In an embodiment, W is halogen, hydroxy, O-p-toluenesulphonyl, O-methanesulphonyl, or O-trifluoromethanesulphonyl.

In a preferred embodiment, W is halogen, O-p-toluenesulphonyl, O-methanesulphonyl, or O-trifluoromethanesulphonyl;

In a more preferred embodiment, W is halogen.

In an embodiment, $R^x$ is $C_1$-$C_6$-alkyl; In a preferred embodiment, $R^x$ is $C_1$-$C_4$-alkyl such as methyl, ethyl, isopropyl, n-propyl, ter-butyl;

In a more preferred embodiment, $R^x$ is ter-butyl.

In another embodiment, $R^x$ is aryl unsubstituted or substituted with halogen.

In preferred embodiment, $R^x$ is unsubstituted aryl.

In another preferred embodiment, $R^x$ is aryl substituted with halogen.

Preferred embodiments regarding the steps (A), (B), (C) and (D), of the invention are described hereinafter.

In general, the reaction steps performed in the steps (A), (B), (C) and (D), as described in detail hereinafter are performed in reaction vessels customary for such reactions, the reactions being carried out in a continuous, semi-continuous or batch wise manner.

In general, the particular reactions will be carried out under atmospheric pressure. The reactions may, however, also be carried out under reduced pressure.

In general products obtained by any of the reaction steps (A), (B), (C), or (D) results in enantiomeric excess. However, enantiomeric excess can be further increased during isolation, purification for example crystallization of an enantiomer, as well as during or after use of the product.

The temperatures and the duration times of the reactions may be varied in broad ranges, which the person skilled in the art knows from analogous reactions. The temperatures often depend on the reflux temperature of the solvents. Other reactions are preferably performed at room temperature, i.e. at about 25° C., or under ice cooling, i.e. at about 0° C. The end of the reaction can be monitored by methods known to a person skilled in the art, e.g. thin layer chromatography or HPLC or GC.

If not otherwise indicated, the molar ratios of the reactants, which are used in the reactions, are in the range of from 0.2:1 to 1:0.2, preferably from 0.5:1 to 1:0.5, more preferably from 0.8:1 to 1:0.8. Preferably, equimolar amounts are used.

If not otherwise indicated, the reactants can in principle be contacted with one another in any desired sequence.

The person skilled in the art knows when the reactants or reagents are moisture sensitive, so that the reaction should be carried out under inert gases such as under a nitrogen atmosphere, and dried solvents should be used.

The person skilled in the art also knows the best work-up of the reaction mixture after the end of the reaction.

In the following, preferred embodiments regarding step (A) of the invention are provided. It is to be understood that the preferred embodiments mentioned above and those still to be illustrated below of step (A) of the invention are to be understood as preferred alone or in combination with each other.

In one embodiment, the hydrogen source is hydrogen source selected from b) mixture of $N(R)_3$, wherein R is H or $C_1$-$C_6$-alkyl, and HCOOH, c) HCOONa, and d) mixture of isopropyl alcohol and t-BuOK or t-BuONa or t-BuOLi;

In one embodiment, the hydrogen source is hydrogen;

In one embodiment, the hydrogen source is a mixture of $N(R)_3$ and HCOOH.

In an embodiment, R is H;

In another embodiment, R is $C_1$-$C_6$-alkyl

In another embodiment, R is $C_1$-$C_4$-alkyl such as methyl, ethyl, isopropyl, n-propyl, ter-butyl.

In a preferred embodiment, R is H, ethyl, isopropyl, or ter-butyl.

In a more preferred embodiment, R is H or ethyl.

In a most preferred embodiment R is ethyl.

In an embodiment, volume ratio of $N(R)_3$ to HCOOH in the range of 1:2 to 1:10.

In a preferred embodiment, volume ratio of $N(R)_3$ to HCOOH is in the range of 1:1 to 1:4.

In more preferred embodiment, volume ratio of $N(R)_3$ to HCOOH is in the range of 1:1 to 1:3.

In another embodiment, the hydrogen source is HCOONa.

In another embodiment, the hydrogen source is HCOOK.

In another embodiment, the hydrogen source is mixture of isopropyl alcohol, and t-BuOK.

In another embodiment, the hydrogen source is mixture of isopropyl alcohol, and t-BuONa.

In an embodiment, m is 0;

In an embodiment, m is 1;

In an embodiment, the hydrogenation catalyst is MXLn(η-arene)$_m$ wherein m is 1 and η-arene is aryl ring which is unsubstituted or substituted with $C_1$-$C_4$-alkyl.

In an embodiment, the hydrogenation catalyst is MXLn(η-arene)$_m$ wherein m is 1 and η-arene is selected from benzene, p-cymene, mesitylene, 2,4,6-triethylbenzene, hexamethylbenzene, anisole, 1,5-cyclooctadiene, cyclopentadienyl (Cp), norbornadiene, and pentamethylcyclopentadienyl (Cp*).

In an embodiment, the hydrogenation catalyst is MXLn (η-arene)$_m$ wherein m is 1 and η-arene is selected from benzene, p-cymene, mesitylene, 2,4,6-triethylbenzene, hexamethylbenzene, anisole, 1,5-cyclooctadiene, cyclopentadienyl (Cp), and pentamethylcyclopentadienyl (Cp*).

In another embodiment, the hydrogenation catalyst is MXLn(η-arene)$_m$ wherein m is 1 and η-arene is selected from cyclopentadienyl (Cp), and pentamethylcyclopentadienyl (Cp*).

In another embodiment, the hydrogenation catalyst is MXLn(η-arene)$_m$ wherein m is 1 and η-arene is cyclopentadienyl (Cp).

In another embodiment, the hydrogenation catalyst is MXLn(η-arene)$_m$ wherein m is 1 and η-arene is pentamethylcyclopentadienyl (Cp*).

In another embodiment, the hydrogenation catalyst is MXLn(η-arene)$_m$ wherein m is 1 and η-arene is selected from benzene, p-cymene, mesitylene, 2,4,6-triethylbenzene, hexamethylbenzene, anisole, and 1,5-cyclooctadiene.

In an embodiment, X is an anion formed by reacting the M or MLn with an acid of the corresponding anion, preferably of hydrochloric acid, hydrobromic acid, hydroiodic acid, Tetra-fluoroboric acid, or hexafluorophosphoric acid.

In another embodiment, X is selected from halides, hexafluorosilicate, hexafluorophosphate, benzoate, sulfonate, and the anions of $C_1$-$C_6$-alkanoic acids, preferably formate, acetate, propionate and butyrate.

In another embodiment, X is halide selected from chloride, bromide, and iodide.

In another embodiment, X is chloride or bromide.

In another embodiment, X is chloride.

In another embodiment, X is tetrafluoroborate.

In another embodiment, Ln is Ln1 wherein $R^{10}$ is NH—$SO_2$—$R^{11}$ and wherein $R^{12}$ and $R^{11}$ independently are unsubstituted or substituted aryl.

In another embodiment, Ln is Ln1 wherein $R^{10}$ is NH—$SO_2$—$R^{11}$ and wherein $R^{12}$ and $R^{11}$ independently are substituted aryl.

In another embodiment, Ln is Ln1 wherein $R^{10}$ is NH—$SO_2$—$R^{11}$ and wherein $R^{12}$ and $R^{11}$ independently are unsubstituted aryl.

In another embodiment, Ln is Ln1 wherein $R^{10}$ is NH—$SO_2$—$R^{11}$ and wherein $R^{11}$ is substituted aryl and $R^{12}$ is $C_6$-$C_{10}$-cycloalkyl.

In another embodiment, Ln is Ln1 and wherein $R^{10}$ is NH—$SO_2$—$R^{11}$; and wherein $R^{11}$ is substituted aryl and $R^{12}$ is unsubstituted aryl.

In another embodiment, Ln is Ln1 and wherein $R^{10}$ is NH—$SO_2$—$R^{11}$; and wherein $R^{11}$ is unsubstituted aryl and $R^{12}$ is substituted aryl.

In another embodiment, Ln is Ln1 wherein $R^{10}$ is NH—$SO_2$—$R^{11}$ and wherein $R^{11}$ unsubstituted or substituted aryl and both $R^{12}$ are linked together to form a 3- to 6-membered carbocyclic ring or a 5- to 10-membered partially unsaturated carbocyclic ring.

In another embodiment, MXLn(η-arene)$_m$ is MXLn1(η-arene)$_m$ and wherein $R^{10}$ is NH—$SO_2$—$R^{11}$; and $R^{12}$ and $R^{11}$ independently are phenyl which are unsubstituted or substituted with 1 or 2 substituents selected from halogen, $C_1$-$C_4$-alkyl, $C_1$-$C_4$-alkoxy, $C_3$-$C_6$-cycloalkyl, $SO_3H$, and $SO_3Na$.

In another embodiment, MXLn(η-arene)$_m$ is MXLn1(η-arene)$_m$ and wherein X is halide; R$^{12}$ independently is phenyl, 2-methylphenyl, 3-methylphenyl, 4-methylphenyl or 4-methoxyphenyl;

R$^{10}$ is NH—SO$_2$—R$^{11}$ and —SO$_2$—R$^{11}$ is p-toluenesulfonyl, methanesulfonyl, 4-benzenesulfonyl, 4-tri-fluoromethylphenyl-sulfonyl or pentafluorophenyl-sulfonyl.

In another embodiment, Ln is Ln1 wherein R$^{10}$ is OH and R$^{12}$ is unsubstituted or substituted aryl.

In another embodiment, Ln is Ln1 wherein R$^{10}$ is OH and R$^{12}$ is substituted aryl.

In another embodiment, Ln is Ln1 wherein R$^{10}$ is OH and R$^{12}$ is unsubstituted aryl.

In another embodiment, Ln is Ln1 wherein R$^{10}$ is OH and R$^{12}$ is C$_6$-C$_{10}$-cycloalkyl.

In another embodiment, Ln is Ln1 wherein R$^{10}$ is OH and both R$^{12}$ are linked together to form a 3- to 6-membered carbocyclic ring or a 5- to 10-membered partially unsaturated carbocyclic ring.

In another embodiment Ln1 is supported on silica gel, dendrimers, polystyrenes or mesoporous siliceous foam, For example as described in Haraguchi, N., Tsuru, K., Arakawa, Y., Isuno, S. *Org. Biomol. Chem.* 2009, 7, 69.

In an embodiment, M is rhodium, ruthenium, iridium, platinum, palladium, iron or nickel.

In another embodiment, M is rhodium, ruthenium, iridium, or platinum.

In another embodiment, M is rhodium, ruthenium, or platinum.

In another embodiment, M is rhodium, iridium, or platinum.

In another embodiment, M is rhodium, ruthenium, or iridium.

In another embodiment, M is rhodium or ruthenium.

In another embodiment, M is rhodium or iridium.

In another embodiment, M is ruthenium or iridium.

In another embodiment, M is palladium, iron or nickel.

In another embodiment, M is palladium or nickel.

In another embodiment, M is, iron or nickel.

In another embodiment, M is palladium or iron.

In a preferred embodiment, M is rhodium.

In another preferred embodiment, M is ruthenium.

In another preferred embodiment, M is iridium.

In another preferred embodiment, M is palladium.

In another preferred embodiment, M is iron.

In another preferred embodiment, M is nickel.

In another preferred embodiment, M is platinum.

In another embodiment, m is 1 and MXLn(η-arene)$_m$ is of the formula MXLnCp*, wherein M is rhodium, ruthenium, iridium, platinum, palladium, iron or nickel.

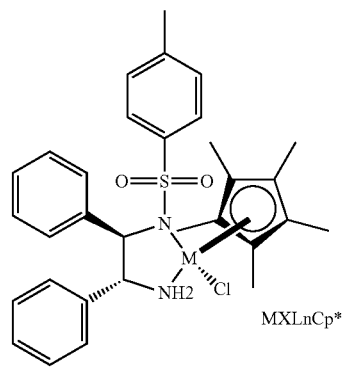

MXLnCp*

In another embodiment, Ln is Ln2 which is a chiral phosphorous ligand.

In another embodiment, the chiral phosphorous ligand Ln2 is selected from chiral monodentate or bidentate, phosphine or phosphite ligands.

In another embodiment, the chiral phosphorous ligand Ln2 is selected from ligands listed in below Table-A or selected from their corresponding enantiomers.

TABLE-A

| Sr. No. | Structure | Name |
|---|---|---|
| 1. | 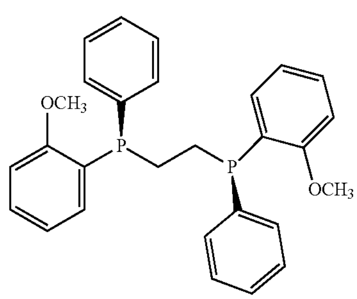 [SMILES: COc1ccccc1[P@](CC[P@](c1ccccc1)c1ccccc1OC)c1ccccc1] | (R,R)-DIPAMP |
| 2. | 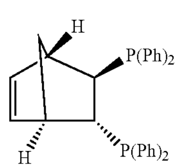 | (R,R)-NORPHOS |

TABLE-A-continued

| Sr. No. | Structure | Name |
|---|---|---|
| 3. | 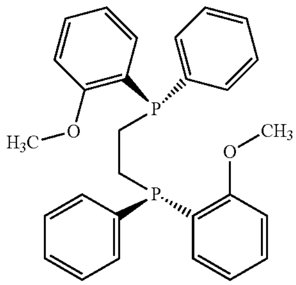 | (S,S)-DIPAMP |
| 4. | 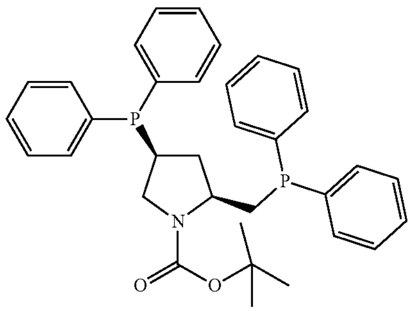 [SMILES: CC(C)(C)OC(=O)N1C[C@@H](P(c2ccccc2)c2ccccc2)C[C@H]1CP(c1ccccc1)c1ccccc1] | (S,S)-BPPM |
| 5 | 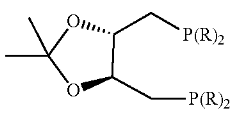 | (S,S)-DIOP: R = Ph (S,S)-Cy-DIOP: R = Cy (S,S)-MOD-DIOP: R = 3,5-(CH₃)₂-4-(CH₃O)C₆H₂ |
| 6 | 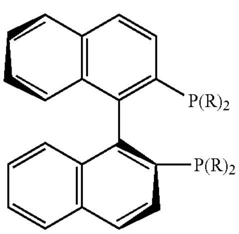 | (S)-BINAP: R = Ph (S)-TolBINAP: R = 4-CH₃C₆H₄ (S)-XylBINAP: R = 3,5-(CH₃)2-C₆H₃ |
| 7 | 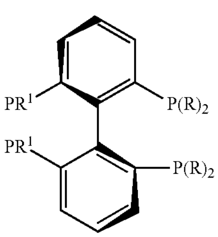 | (S)-BICHEP: R = Cy; R¹ = CH₃ (S)-BIPHEMP: R = Ph; R¹ = CH₃ (S)-BICHEP: R = Ph; R¹ = OCH₃ |
| 8 | 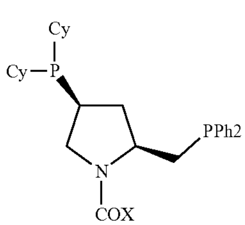 | (S,S)BCPM: X = OC(CH₃)₃ (S,S)-MCCPM: X = NHCH₃ |

TABLE-A-continued

| Sr. No. | Structure | Name |
|---|---|---|
| 9 | 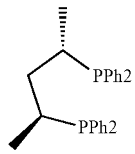 | (S,S)-BDPP |
| 10 | 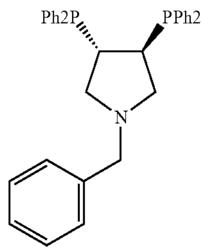 | (S,S)-PYRPHOS |
| 11 | 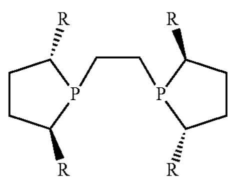 | (S,S)-Me-BPE: R = CH$_3$<br>(S,S)-Et-BPE: R = C$_2$H$_5$<br>(S,S)-iPr-BPE: R = CH(CH$_3$)$_2$ |
| 12 | 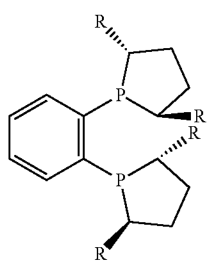 | (S,S)-Me-DuPhos: R = CH$_3$<br>(S,S)-Et-DuPhos: R = C$_2$H$_5$<br>(S,S)-iPr-DuPhos: R = CH(CH$_3$)$_2$ |
| 13 | 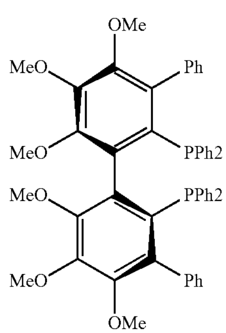 | (S)-o-Ph-HexaMeO-BIPHEP |
| 14 | 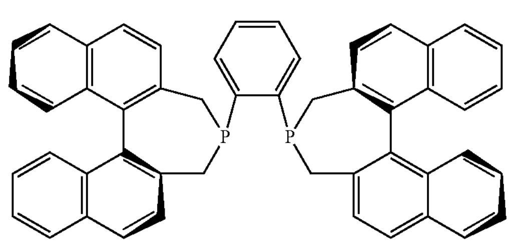 | (S,S)BINAPHANE |

TABLE-A-continued

| Sr. No. | Structure | Name |
|---|---|---|
| 15 | 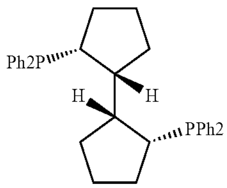 | (R,R)-BCIP |
| 16 | 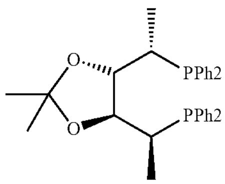 | (R,S,S,R)-DIOP* |
| 17 | 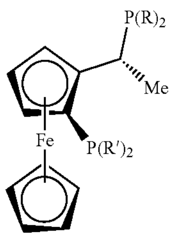 | (R)-(S)-Josiphos: R = Cy, R' = Ph<br>(R)-(S)-PPF-t-Bu$_2$: R = t-Bu, R' = Ph<br>(R)-(S)-Xyliphos: R = 3,5-Me$_2$-C$_6$H$_3$, R' = Ph<br>(R)-(S)-Cy$_2$PF-PCy$_2$: R = R' = Cy |
| 18 | 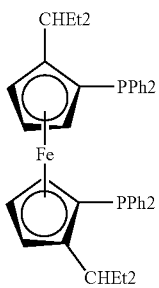 | (S,S)-FerroPHOS |
| 19 | 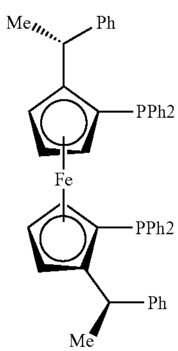 | FERRIPHOS |
| 20 | 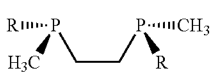 | (S,S)-BisP*<br>(S,S)-tBu-BisP*: R = tBu<br>(S,S)-Ad-BisP*: R = 1-adamantyl<br>(S,S)-Cy-BisP*: R = Cy |
| 21 | 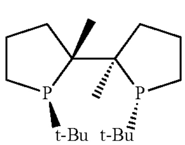 [SMILES: CC(C)(C)[P@@]1CCC[C@]1(C)[C@@]1(C)CCC[P@]1C(C)(C)C] | (S,S,R,R)-TangPhos |

TABLE-A-continued

| Sr. No. | Structure | Name |
|---|---|---|
| 22 | 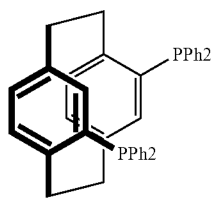 | (S)-[2,2]-PHENOPHOS |
| 23 | 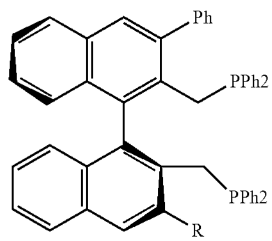 | (S)-Ph-o-NAPHOS |
| 24 | 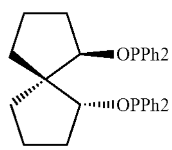 | (R)-spirOP |
| 25 | 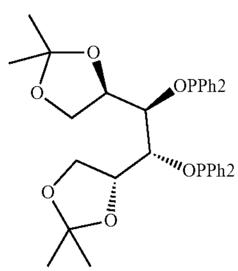 | DIMOP |
| 26 | 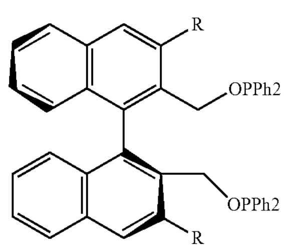 | BINAPO: R = H<br>(S)-Ph-o-BIN-APO: R = Ph |
| 27 | 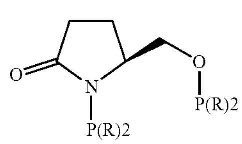 | (S)-Cy,Cy-ox-oProNOP: R = Cy<br>(S)-Cp,Cp-ox-oProNOP: R = Cp |
| 28 | 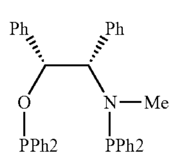 | (1R,2S)-DPAMPP |

TABLE-A-continued

| Sr. No. | Structure | Name |
|---|---|---|
| 29 | (structure with NHPAr2 groups on binaphthyl) | (R)-BDPAB: Ar = Ph (R)-Xyl-BDP: Ar = 3,5-(CH$_3$)$_2$-C$_6$H$_3$ |
| 30 | (structure with NHPPh2 groups on octahydrobinaphthyl) | (R)-H$_8$-BDPAB | wherein Cy = cyclohexyl and Ph = phenyl.

In another embodiment, the chiral phosphorous ligand is selected from (R)-BINAP, (S)-BINAP, (R)ToIBINAP, (S)-ToIBINAP, (R,R)-DIPAMP, (S,S)-DIPAMP, (1R,2S)—(R)—(S)-Josiphos, or selected from their corresponding enantiomers.

In an embodiment, molar ratio of the compound of formula III to MXLn(η-arene)$_m$ is in the range of 1:0.0001 to 1:0.001.

In a preferred embodiment, molar ratio of the compound of formula III to MXLn(η-arene)$_m$ is in the range of 1:0.001 to 1:0.01.

In a more preferred embodiment, molar ratio of the compound of formula III to MXLn(η-arene)$_m$ is in the range of 1:0.001 to 1:0.05.

In an embodiment, reaction temperature of the hydrogenation in step (A) is kept within a range of from 0 to 120° C., preferably in the range of from 0 to 85° C., preferably in the range of from 20 to 85° C., more preferably in the range of from 20° to 50° C., also more preferably in the range of from 0° to 30° C., also more preferably at 0° C.

In an embodiment, reaction of the hydrogenation in step (A) is carried out at a temperature below 0° C.

In an embodiment, the hydrogenation in step (A) is carried out in the absence of solvent.

In another embodiment, the hydrogenation in step (A) is carried out in a solvent.

Suitable solvents include water and aliphatic hydrocarbons such as pentane, hexane, cyclohexane and petroleum ether; aromatic hydrocarbons such as toluene, o-, m- and p-xylene; halogenated hydrocarbons such as methylene chloride, chloroform, 1,2-dichloroethane and chlorobenzene; alcohols such as methanol, ethanol, n-propanol, iso-propanol, n-butanol and tert-butanol; ketones such as acetone, 2-butanone; C$_2$-C$_4$-alkandiols, such as ethylene glycol or propylene glycol; ether alkanols such as diethylene glycol; carboxylic esters such as ethyl acetate; N-methylpyrrolidone; dimethylformamide; dimethyl acetamide; and ethers including open-chained and cyclic ethers, especially diethyl ether, methyl-tert-butyl-ether (MTBE), 2-methoxy-2-methylbutane, cyclopentylmethylether, 1,4-dioxane, tetrahydrofuran, and 2-methyltetrahydrofuran, in particular tetrahydrofuran, MTBE, and 2-methyltetrahydrofuran. Mixtures of said solvents can also be used.

In a preferred embodiment, solvent is selected from water, C$_2$-C$_6$-alkandiols, C$_1$-C$_6$-haloalkanes, halobenzene, carboxylic esters, N-methylpyrrolidone; dimethylformamide; dimethyl acetamide and ethers including open-chained and cyclic ethers, or mixture of the two or more thereof.

In another preferred embodiment, solvent is selected from water, dimethylformamide, toluene, tetrahydrofuran, N-methylpyrrolidone, dimethyl acetamide, or mixture of the two or more thereof.

In an embodiment, the volume ratio of the compound of formula V to the solvent is in the range of 1:40 to 1:0.

In another embodiment, the volume ratio of compound of formula V to the solvent is in the range of 1:30 to 1:5.

In a preferred embodiment, the volume ratio of compound of formula V to the solvent is in the range of 1:20 to 1:10, preferably 1:1.

The reaction times in the step (A) may vary over a broad range. Preferred reaction times are in the range of 5 mins to 1 day, preferably from 15 mins to 6 hours, more preferably in the range of from 15 mins. to 3 hours, e.g. 1 to 2 hours.

In an embodiment, the step (A) can be carried out in the presence of surfactants N(R$^s$)$_4$X$^a$ wherein R$^s$ is independently C$_1$-C$_{22}$ alkyl, C$_1$-C$_{22}$ cycloalkyl, or aryl which is unsubstituted or substituted with halogen, and X$^a$ is chloro, bromo, iodo, hydrogen sulfate, hexafluorophosphate, acetate, benzoate or tetrafluoroborate.

It is further preferred that the reaction is performed in a protective or inert gas atmosphere, e.g. under nitrogen or Argon.

It is further preferred that the reaction is performed under reduced pressure.

In another embodiment the reaction is performed in hydrogen gas atmosphere.

In a preferred embodiment, the compound of formula VI obtained by step (A) in >80% enantiomeric excess.

In the following, preferred embodiments regarding step (B) of the invention are provided. It is to be understood that the preferred embodiments mentioned above and those still to be illustrated below of step (B) of the invention are to be understood as preferred alone or in combination with each other.

In an embodiment, the step (B) is carried out in the presence of an acid;

In an embodiment, suitable acids are in general Inorganic acids such as hydrofluoric acid, hydrochloric acid, hydrobromic acid, hydroiodic acid, sulphuric acid, phosphoric acid, perchloric acid, or mixture of one or more thereof.

In a preferred embodiment, the acid is hydrochloric acid, sulphuric acid, phosphoric acid, hydroiodic acid, or mixture of one or more thereof.

In another embodiment, suitable acids are Lewis acids, such as boron tri fluoride, aluminium tri chloride, iron (III) chloride, tin (IV) chloride, titanium (IV) chloride, and zinc (II) chloride.

In another embodiment, suitable acids are in general organic acids such as formic acid, $C_1$-$C_8$-alkyl-$(COOH)_y$, or $C_1$-$C_8$-haloalkyl-$(COOH)_y$, wherein y is 1 or 2; $CH_3SO_3H$, citric acid, oxalic acid, p-toluenesulphonic acid acetic acid, propionic acid, oxalic acid, toluene sulphonic acid, benzene sulphonic acid, camphor sulphonic acid, citric acid, and trifluoro acetic acid, or mixture of one or more thereof.

In a preferred embodiment, the acid is $C_1$-$C_8$-alkyl-$(COOH)_y$, $C_1$-$C_8$-haloalkyl-$(COOH)_y$, wherein y is 1 or 2, $CH_3SO_3H$, citric acid, oxalic acid, p-toluenesulphonic acid, or mixture of two or more thereof.

In another embodiment, the acid in step (B) is selected from hydrochloric acid, sulphuric acid, phosphoric acid, polyphosphoric acid, hydroiodic acid, $C_1$-$C_8$-alkyl-$(COOH)_y$, $C_1$-$C_8$-haloalkyl-$(COOH)y$, $CH_3SO_3H$, citric acid, oxalic acid, p-toluenesulphonic acid, or mixture of two or more thereof; wherein y is 1 or 2.

In a particularly preferred embodiment, the acid in step (B) is hydrochloric acid.

In a preferred embodiment, when $R^A$ in the compound of formula VI is $S(=O)_2R^x$, the step (B) is carried out in the presence of an acid.

The acids are generally employed in equimolar amounts; however, they can also be used in catalytic amounts, in excess or, if appropriate, as solvent.

In another embodiment, the step (B) is carried out in the presence of an acid and a buffer.

Buffers include aqueous and non-aqueous buffers, and are preferably non-aqueous buffers. Preferred buffers include buffers based on acetate, phosphate or formate, e.g. sodium acetate, potassium hydrogen phosphate, potassium dihydrogen phosphate, or ammonium formate.

In another embodiment, wherein the step (B) carried out in the presence of an acid further comprises metal such as palladium or platinum, preferably palladium, and hydrogen gas. In an embodiment, the step (B) is carried out in the presence of a base.

Suitable bases are, in general, inorganic compounds, such as alkali metal and alkaline earth metal hydroxides, such as lithium hydroxide, sodium hydroxide, potassium hydroxide and calcium hydroxide, alkali metal and alkaline earth metal oxides, such as lithium oxide, sodium oxide, calcium oxide, and magnesium oxide, alkali metal and alkaline earth metal carbonates, such as lithium carbonate, potassium carbonate and calcium carbonate.

In one particularly preferred embodiment, the base is selected from alkali metal and alkaline earth metal hydroxides, in particular from the group consisting of lithium hydroxide, sodium hydroxide, magnesium hydroxide, potassium hydroxide, and calcium hydroxide.

In another particularly preferred embodiment, the base is selected from alkali metal and alkaline earth metal oxides, in particular from the group consisting of lithium oxide, sodium oxide, calcium oxide, and magnesium oxide.

The bases are generally employed in equimolar amounts; however, they can also be used in catalytic amounts or in excess.

In an embodiment, the reaction temperature in step (B) is kept within a range of from 0 to 120° C., preferably in the range of from 20 to 100° C., more preferably in the range of from 20° to 60° C.

In an embodiment the hydrolysis in step (B) is carried out in the absence of a solvent.

In another embodiment the hydrolysis in step (B) is carried out in a solvent.

Suitable solvents include water and aliphatic hydrocarbons such as pentane, hexane, cyclohexane and petroleum ether; aromatic hydrocarbons such as toluene, o-, m- and p-xylene; halogenated hydrocarbons such as methylene chloride, chloroform, 1,2-dichloroethane and chlorobenzene; alcohols such as methanol, ethanol, n-propanol, isopropanol, n-butanol and tert-butanol; ketones such as acetone, 2-butanone; $C_2$-$C_4$-alkandiols, such as ethylene glycol or propylene glycol; ether alkanols such as diethylene glycol; carboxylic esters such as ethyl acetate; N-methylpyrrolidone; dimethylformamide; and ethers including open-chained and cyclic ethers, especially diethyl ether, methyl-tert-butyl-ether (MTBE), 2-methoxy-2-methylbutane, cyclopentylmethylether, 1,4-dioxane, tetrahydrofuran, and 2-methyltetrahydrofuran, in particular tetrahydrofuran, MTBE, and 2-methyltetrahydrofuran. Mixtures of said solvents can also be used.

In another embodiment, the solvent is selected from $C_1$-$C_6$-alcohol, water, $C_2$-$C_6$-alkandiols, carboxylic esters, N-methylpyrrolidone, dimethylformamide, and ethers including open-chained and cyclic ethers, or mixture of the two or more thereof.

In another embodiment, the solvent is selected from water, dimethylformamide, N-methylpyrrolidone, methyl-tert-butyl-ether, methanol, ethanol, isopropanol, or mixture of two or more thereof.

Preferred solvents are protic solvents, preferably alcohols selected from the group consisting of such as methanol, ethanol, n-propanol, isopropanol, n-butanol and tert-butanol.

In a preferred embodiment, the solvent is a $C_1$-$C_4$-alcohol, in particular methanol.

In an embodiment, the volume ratio of the compound of formula VI to solvent is in the range of 1:30 to 1:0.

In another embodiment, the volume ratio of the compound of formula VI to solvent is in the range of 1:20 to 1:10.

In a preferred embodiment, the volume ratio of the compound of formula VI to solvent is in the range of 1:10 to 1:0.

In a preferred embodiment, the compound of formula VII obtained by step (B) in >80% enantiomeric excess.

In the following, preferred embodiments regarding step (C) of the invention are provided. It is to be understood that the preferred embodiments mentioned above and those still to be illustrated below of step (C) of the invention are to be understood as preferred alone or in combination with each other.

In an embodiment, the step (C) is carried out in the presence of a base;

Suitable bases are, in general, inorganic compounds, such as alkali metal and alkaline earth metal hydroxides, such as lithium hydroxide, sodium hydroxide, potassium hydroxide and calcium hydroxide, alkali metal and alkaline earth metal oxides, such as lithium oxide, sodium oxide, calcium oxide, and magnesium oxide, alkali metal and alkaline earth metal hydrides, such as lithium hydride, sodium hydride, potassium hydride and calcium hydride, alkali metal and alkaline earth metal carbonates, such as lithium carbonate, potassium carbonate and calcium carbonate, and also alkali metal bicarbonates, such as sodium bicarbonate, moreover organic bases, for example tertiary amines, such as trimethylamine, triethylamine, triisopropylethylamine and N-methylpiperidine, pyridine, substituted pyridines, such as collidine, lutidine and 4-dimethylaminopyridine, and also bicyclic amines.

In one particularly preferred embodiment, the base is selected from alkali metal and alkaline earth metal hydroxides, in particular from the group consisting of lithium hydroxide, sodium hydroxide, magnesium hydroxide, potassium hydroxide, and calcium hydroxide.

In another particularly preferred embodiment, the base is selected from alkali metal and alkaline earth metal oxides, in particular from the group consisting of lithium oxide, sodium oxide, calcium oxide, and magnesium oxide.

In another particularly preferred embodiment, the base is selected from alkali metal and alkaline earth metal hydrides, in particular from the group consisting of lithium hydride, sodium hydride, potassium hydride, and calcium hydride.

In another particularly preferred embodiment, the base is selected from alkali metal amides, in particular from the group consisting of lithium amide, sodium amide, and potassium amide In another particularly preferred embodiment, the base is selected from alkali metal and alkaline earth metal carbonates, in particular from the group consisting lithium carbonate and calcium carbonate.

In another particularly preferred embodiment, the base is selected from alkali metal bicarbonates, and is preferably sodium bicarbonate.

In another particularly preferred embodiment, the base is selected from alkali metal alkyls, in particular from the group consisting of methyllithium, butyllithium, and phenyllithium.

In another particularly preferred embodiment, the base is selected from alkylmagnesium halides, and is preferably isopropylmagnesiumchloride.

In another particularly preferred embodiment, the base is selected from trimethylamine, triethylamine, triisopropylethylamine and N-methylpiperidine, pyridine, substituted pyridines, such as collidine, lutidine and 4-dimethylaminopyridine, and also bicyclic amines.

In more particularly preferred embodiment, the base is trimethylamine or triethylamine.

The bases are generally employed in equimolar amounts; however, they can also be used in catalytic amounts, in excess or, if appropriate, as solvent.

In an embodiment, the reaction temperature hydrolysis in step (C) is kept within a range of from 0 to 130° C., preferably in the range of from 20 to 85° C., more preferably in the range of from 20° to 60° C.

In an embodiment step (C) is carried out in the absence of solvent.

In another embodiment, the step (C) is carried out in a solvent.

Suitable solvents include water and aliphatic hydrocarbons such as pentane, hexane, cyclohexane and petroleum ether; aromatic hydrocarbons such as toluene, o-, m- and p-xylene; halogenated hydrocarbons such as methylene chloride, chloroform, 1,2-dichloroethane and chlorobenzene; alcohols such as methanol, ethanol, n-propanol, isopropanol, n-butanol and tert-butanol; ketones such as acetone or 2-butanone; $C_2$-$C_4$-alkandiols, such as ethylene glycol or propylene glycol; ether alkanols such as diethylene glycol; carboxylic esters such as ethyl acetate; N-methylpyrrolidone; dimethylformamide; and ethers including open-chained and cyclic ethers, especially diethyl ether, methyl-tert-butyl-ether (MTBE), 2-methoxy-2-methylbutane, cyclopentyl methylether, 1,4-dioxane, tetrahydrofuran, and 2-methyltetrahydrofuran, in particular tetrahydrofuran, MTBE, and 2-methyltetrahydrofuran. Mixtures of said solvents can also be used.

In another embodiment, the solvent is selected from $C_1$-$C_6$-alcohol, water, $C_2$-$C_6$-alkandiols, carboxylic esters, N-methylpyrrolidone, dimethylformamide, and ethers including open-chained and cyclic ethers, or mixture of the two or more thereof.

In another embodiment, the solvent is selected from water, dimethylformamide, N-methylpyrrolidone, methyl-tert-butyl-ether, methanol, ethanol, isopropanol, or mixture of two or more thereof.

Preferred solvents are protic solvents, preferably alcohols selected from the group consisting of such as methanol, ethanol, n-propanol, isopropanol, n-butanol and tert-butanol.

In a preferred embodiment, the solvent is a $C_1$-$C_4$-alcohol, in particular ethanol.

In an embodiment, the volume ratio of the compound of formula VII to solvent is in the range of 1:30 to 1:0.

In another embodiment, the volume ratio of the compound of formula VII to solvent is in the range of 1:20 to 1:5.

In a preferred embodiment, the volume ratio of the compound of formula VII to solvent is in the range of 1:20 to 1:10.

In a preferred embodiment, the compound of formula VIII obtained by step (C) in >80% enantiomeric excess.

In the following, preferred embodiments regarding step (D) of the invention are provided. It is to be understood that the preferred embodiments mentioned above and those still to be illustrated below of step (D) of the invention are to be understood as preferred alone or in combination with each other.

In an embodiment, LG is $OR^u$;

In another embodiment, LG is $SR^u$;

In an embodiment, $R^u$ is unsubstituted $C_1$-$C_6$-alkyl;

In another embodiment, $R^u$ is $C_1$-$C_6$-alkyl, which is substituted with halogen;

In another embodiment, $R^u$ is unsubstituted aryl;

In another embodiment, $R^u$ is aryl which is substituted with halogen;

In an embodiment, the reaction temperature in step (D) is kept within a range of from 0 to 130° C., preferably in the range of from 20 to 100° C., more preferably in the range of from 70° to 110° C.

In an embodiment step (D) is carried out in the absence of solvent.

In another embodiment step (D) is carried out in a solvent.

Suitable solvents include aliphatic hydrocarbons such as hexane, heptane, cyclohexane and petroleum ether; aromatic hydrocarbons such as toluene, o-, m- and p-xylene; halogenated hydrocarbons such as methylene chloride, chloroform, 1,2-dichloroethane and chlorobenzene; alcohols such as methanol, ethanol, n-propanol, isopropanol, n-butanol and tert-butanol; ketones such as acetone or 2-butanone, $C_2$-$C_4$-alkandiols, such as ethylene glycol or propylene glycol; ether alkanols such as diethylene glycol; carboxylic esters such as ethyl acetate; N-methylpyrrolidone; dimethylformamide; and ethers including open-chained and cyclic ethers, especially diethyl ether, methyl-tert-butyl-ether (MTBE), 2-methoxy-2-methylbutane, cyclopentyl methylether, 1,4-dioxane, tetrahydrofuran, and 2-methyltetrahydrofuran, in particular tetrahydrofuran, MTBE, and 2-methyltetrahydrofuran. Mixtures of said solvents can also be used.

In another embodiment, the solvent is selected from dimethylformamide, N-methylpyrrolidone, toluene, xylene, monochlorobenzene, or mixture of two or more thereof.

Preferred solvents are aromatic hydrocarbons, preferably toluene, o-, m- and p-xylene, monochlorobenzene In a preferred embodiment, the solvent is toluene.

In an embodiment, the volume ratio of reactants to solvent is in the range of 1:40 to 1:0.

In another embodiment, the volume ratio of reactants to solvent is in the range of 1:40 to 1:5.

In a preferred embodiment, the volume ratio of reactants to solvent is in the range of 1:30 to 1:10.

In a preferred embodiment, the volume ratio of reactants to solvent is in the range of 1:20 to 1:10, preferably 1:5.

In a preferred embodiment, the compound of formula X obtained by step (D) in >80% enantiomeric excess.

In more preferred embodiment, the compound of formula X obtained by step (D) in >95% enantiomeric excess.

In another embodiment of the invention, a process for preparing a compound of formula X having below stereochemistry as in formula X—R or a process for preparing a compound of formula X with enantiomeric excess of R-enantiomer i.e. compound X—R,

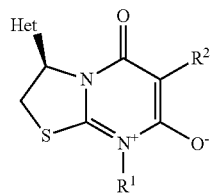

X-R wherein Het, $R^1$ and $R^2$ are as defined herein;
comprising at least the steps of,
(A) hydrogenation of a compound of formula V,

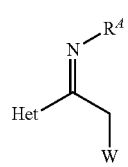

V wherein Het, $R^4$ and W are as defined herein;
in the presence of a hydrogenation catalyst MXLnCp* wherein M is rhodium, ruthenium, iridium, palladium, iron, platinum, or nickel,

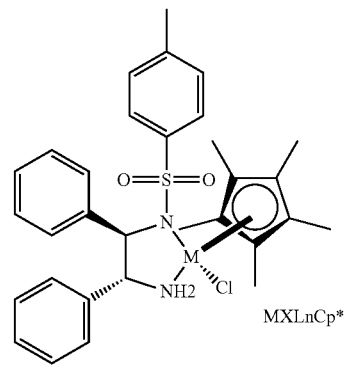

MXLnCp* and a hydrogen source selected from a)hydrogen, b) mixture of $N(R)_3$ wherein R is H or $C_1$-$C_6$-alkyl, and HCOOH, c) HCOONa or HCOOK, d) mixture of $C_1$-$C_8$-alcohol and t-BuOK, t-BuONa, or t-BuOLi, and e) combination of two or more from a) to d);
to obtain a compound of formula VI having below stereochemistry as in formula VI-S,

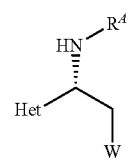

VI-S wherein Het, $R^4$ and W are as defined in the compound of formula V;
(B) hydrolyzing the compound of formula VI-S as defined herein, in the presence of an acid or a base,
to obtain a compound of formula VII having below stereochemistry as in formula VII-S, wherein Het and W are as defined in the compound of formula VI-S;

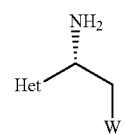

VII-S (C) reacting the compound of formula VII-S with $R^1$NCS, wherein $R^1$ is as defined herein,
in the presence of a base,
to obtain a compound of formula VIII having below stereochemistry as in formula VIII-R,

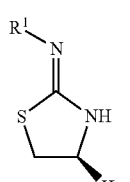

VIII-R wherein Het and W are as defined in the compound of formula VII-S;

(D) reacting the compound of formula VIII—R with a compound of formula IX,

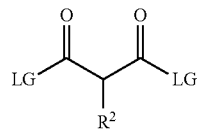

wherein LG and R² are as defined herein,
to obtain the compound of formula X—R.

EXAMPLES

The characterization can be done by coupled High Performance Liquid Chromatography/mass spectrometry (HPLC/MS), Gas chromatography (GC), by NMR or by their melting points.

HPLC method 1: Agilent Eclipse Plus C18, 150 mm×4.6 mm ID×5 um

Gradient A=0.1% TFA in Water, B=0.1% TFA in Acetonitrile.

Flow=1.4 ml/min., column oven temperature=30 C

Gradient program=10% B-100% B—5 min, hold for 2 min, 3 min—10% B.

Run Time=10 min

LCMS method 1: C18 Column (50 mm×3.0 mm×3μ)

Gradient A=10 Mm Ammonium formate in water, B=0.1% Formic acid in acetonitrile

Flow=1.2 ml/min., column oven temperature=40° C.

Gradient program=10% B to 100% B in 1.5 min., hold for 1 min 100% B, 1 min—10% B Run time: 3.75 min Chiral HPLC method 1: ChiralPak IA column, 150 mm×4.6 mm×5μ

Mobile phase A=heptane, B=isopropanol,

Flow=1.0 ml/min, column oven temperature=40° C.

Gradient program=5% B Isocratic; run time: 20 min

Chiral HPLC method 2: ChiralPak IC column, 150 mm×4.6 mm×5μ

Mobile phase A=0.1% diethylamine in heptane, B=0.1% diethylamine in isopropanol, Flow=1.0 ml/min, column oven temperature=40° C.

Gradient program=15% B Isocratic; run time: 20 min

Chiral HPLC method 3: ChiralPak IA column, 150 mm×4.6 mm×5μ

Mobile phase A=heptane, B=isopropanol,

Flow=1.0 ml/min, column oven temperature=40° C.

Gradient program=40% B Isocratic; run time: 20 min

¹H-NMR: The signals are characterized by chemical shift (ppm) vs. tetramethylsilane, by their multiplicity and by their integral (relative number of hydrogen atoms given). The following abbreviations are used to characterize the multiplicity of the signals: m=multiplet, q=quartet, t=triplet, d=doublet and s=singlet.

Abbreviations used are: h for hour(s), min for minute(s), rt for retention time, ee for enantiomeric excess, and ambient temperature for 22-27° C.

The present invention is now illustrated in further details by the following examples, without imposing any limitation thereto.

With appropriate modification of the starting materials, the procedures as described in the examples below can be used to obtain further compounds of formula VI, VII, VIII, or X.

Example-1: Preparation of (3R)-3-(2-chlorothiazol-5-yl)-8-methyl-7-oxo-6-phenyl-2,3-dihydrothiazolo[3,2-a]pyrimidin-4-ium-5-olate Step-1: Preparation of 2-chloro-N-methoxy-N-methyl-acetamide A 3 L four necked flask equipped with Teflon-blade stirrer, reflux condenser and thermo-pocket was charged with N-methoxymethanamine hydrochloride (345 g), water (1.6 L) and the resulting reaction mixture was cooled to 0 to −5° C. Then potassium carbonate (1466 g) was added in lots to above reaction mixture followed by the addition of methyl tert-butyl ether (1.4 L). The chloroacetyl chloride (400 g) was dissolved in tert-butyl methyl ether (0.2 L) and added drop wise in to the above kept reaction mixture at −5° C. to 0° C. and the reaction mixture was stirred for 2 h at 0° C. The reaction mixture was allowed to come to ambient temperature and two phases were separated. The organic layer was dried over sodium sulphate, filtered and evaporated to provide 2-chloro-N-methoxy-N-methyl-acetamide as white solid (440 g, 90% yield and 98.0% area purity by HPLC).

Step-2: Preparation of 2-chloro-1-(2-chlorothiazol-5-yl)ethenone

A 5 L, four necked flask equipped with Teflon-blade stirrer, reflux condenser and thermo-pocket was charged with 2-chlorothiazole (250 g), THF (0.75 L) and the resulting reaction mixture was cooled to 0 to −5° C. Then isopropylmagnesium chloride lithium chloride (1.929 L, 1.3 M solution in THF) was added over 0.5 h into the above kept reaction mixture at 0 to −5° C. The reaction mixture was then heated to 40° C. and the reaction was continued at 40° C. for 2 h. The formation of chloro-(2-chlorothiazol-5-yl) magnesium species was confirmed by quenching the small aliquot of the reaction mixture with Iodine and monitoring the formation of 2-chloro-5-iodo-thiazole by GC analysis (96% conversion was observed by GC analysis). The reaction mixture was cooled to 0 to −5° C. and the solution of 2-chloro-N-methoxy-N-methyl-acetamide (343 g) in THF (0.25 L) was added dropwise. The reaction was continued at −5 to 0° C. for 1 h and the reaction progress was monitored by HPLC. The reaction mixture was quenched with 1.5 N aq. HCl solution (1 L) at −5 to 0° C. and then warm to ambient temperature. The two phases were separated and the aqueous phase extracted with methyl tert-butyl ether (2×300 mL). The combined organic layers were dried over sodium sulphate, filtered and evaporated to obtain crude residue. The crude product was dissolved in methyl tert-butyl ether (0.7 L) at ambient temperature and activated charcoal (4 g) and silica (80 g, 60-120 mesh) were added. The slurry was stirred for 0.5 h, filtered through Buchner funnel and washed with methyl tert-butyl ether (0.3 L). The filtrate was evaporated to obtain 2-chloro-1-(2-chlorothiazol-5-yl)ethanone as pale brown colored oil (409 g, 46% area purity by HPLC)

Step-3: Preparation of N-[2-chloro-1-(2-chlorothiazol-5-yl)ethylidene]-2-methyl-propane-2-sulfinamide A 5 L four necked flask equipped with teflon-blade stirrer, reflux condenser and thermo-pocket was charged with 2-chloro-1-(2-chlorothiazol-5-yl)ethanone (409 g, 46 area % purity by HPLC), THF (1.2 L), 2-methylpropane-2-sulfinamide (252.4 g) and Titanium(IV)ethoxide (485 mL) at ambient temperature under nitrogen atmosphere. The resulting mixture was heated to 50° C. and stirred for 2 h. The reaction progress was monitored by HPLC (>95% conversion by HPLC). The reaction was charged with methyl tert-butyl ether (2.4 L), cooled to 0 to 10° C., quenched slowly with 1 N aq. HCl solution (3.6 L) and stirred for 10 min. The two phases were separated and the organic phase was washed with water (2×800 mL). The organic phase was dried over sodium sulphate, filtered and evaporated to obtain crude residue. The crude product was dissolved in methyl tert-butyl ether (1 L) at ambient temperature and activated charcoal (5.5 g) and silica (100 g, 60-120 mesh) were added. The slurry was stirred for 0.5 h, filtered through Buchner funnel and washed with methyl tert-butyl ether (0.3 L). The filtrate was evaporated to obtain N-[2-chloro-1-(2-chlorothiazol-5-yl)ethylidene]-2-methyl-propane-2-sulfinamide as pale brown colored oil (510 g, 68% area purity by HPLC).

Step-4: Preparation of N-[(1S)-2-chloro-1-(2-chlorothiazol-5-yl)ethyl]-2-methyl-propane-2-sulfinamide a) Preparation of Rhodium Catalyst—RhCl[(R,R)-TsDPEN]Cp*

A 250 mL, three necked flask equipped with Teflon-blade stirrer, nitrogen inlet and thermo-pocket was charged with [RhCl₂Cp*]₂ (2.0 g), (1R,2R)—N-p-toluenesulfonyl-1,2-diphenylethylenediamine (2.38 g), dichloromethane (68 mL) and TEA (1.72 ml) under nitrogen atmosphere. The resulting slurry was stirred for 0.5 h at 22-27° C. and distilled water was added (40 mL). The two phases were separated and the organic phase was washed with water (40 mL). The organic phase was dried over sodium sulphate, filtered and evaporated to get brown coloured solid residue. The brown residue was triturated with n-heptane (20 mL), filtered and dried under nitrogen atmosphere to get obtain RhCl [(R,R)-TsDPEN]Cp* as red coloured solid (3.4 g).

b) Preparation of HCOOH-NEt₃ Mixture

In a 2 L, 3 neck round bottom flask Formic acid (275 mL, >=99% w/w) was added and cooled to 0° C. To this, triethylamine 250 mL, >=99% w/w) was added slowly at 0° C. and used immediately in reaction.

c) Preparation of N-[(1S)-2-chloro-1-(2-chlorothiazol-5-yl)ethyl]-2-methyl-propane-2-sulfinamide A 5 L four necked flask equipped with magnetic stirrer, nitrogen inlet and thermo-pocket was charged with dimethylformamide (2.9 L) and degassed with nitrogen for 10 min. Then RhCl[(R,R)-TsDPEN]Cp* (3.63 g) was added under nitrogen atmosphere at 22 to 27° C. To above kept solution, N-[2-chloro-1-(2-chlorothiazol-5-yl)ethylidene]-2-methyl-propane-2-sulfinamide (170 g) dissolved in dimethylformamide (0.51 L), and HCOOH-NEt₃ (425 mL, in a ratio of 1.1:1) solutions were added simultaneously at 22 to 27° C. over a period of 0.5 h and resulting mixture was stirred at 22-27° C. for 2 h. The HPLC showed >97% conversion. The reaction mixture was quenched with water (3.4 L) and extracted with methyl tert-butyl ether (3×1500 mL). The combined organic phase was evaporated to obtain N-[(1S)-2-chloro-1-(2-chlorothiazol-5-yl)ethyl]-2-methyl-propane-2-sulfinamide (180 g, 80% HPLC purity (rt=4.48 & 4.52 min.))

Step-5: Preparation of (1S)-2-chloro-1-(2-chlorothiazol-5-yl)ethanamine

A 1 L three necked flask equipped with magnetic stirrer, nitrogen inlet and thermo-pocket was charged with N-[(1S)-2-chloro-1-(2-chlorothiazol-5-yl)ethyl]-2-methyl-propane-2-sulfinamide (180 g) and 1 N HCl in MeOH (540 mL) at ambient temperature and the reaction mixture was stirred at 22-27° C. for 14 h. The reaction progress was monitored by HPLC. The organic volatiles were removed under vacuum and the residue was triturated with methyl tert-butyl ether (3×300 mL) and organic phase containing methyl tert-butyl ether was separated from pale yellow colored oily residue. The pale yellow colored residue containing (1S)-2-chloro-1-(2-chlorothiazol-5-yl)ethanamine; hydrochloride was neutralized with 1 N aq. NaOH and extracted with MTBE (3×300 ml). The organic phases were dried over sodium sulphate, filtered and evaporated to obtain (1S)-2-chloro-1-(2-chlorothiazol-5-yl)ethanamine as brown colored residue (51 g; 93 area % HPLC purity (rt=2.646 min.) and 72% ee by chiral HPLC method 1).

Step-6: Preparation of (4R)-4-(2-chlorothiazol-5-yl)-N-methyl-thiazolidin-2-imine A 500 mL, three necked flask equipped with magnetic stirrer, reflux condenser and thermo-pocket was charged with (1S)-2-chloro-1-(2-chlorothiazol-5-yl)ethanamine (51 g, 72% ee), ethanol (200 ml), methyl isothiocyanate (28.53 g) and triethylamine (70 ml). The resulting mixture was stirred for 14 h at 22-27° C. The HPLC analysis showed >99% conversion with formation of (4R)-4-(2-chlorothiazol-5-yl)-N-methyl-thiazolidin-2-imine. Then organic volatiles were removed under vacuum and sodium hydroxide (26 g) and water (200 mL) were added into the reaction flask. The reaction mixture was heated to 100° C. and stirred for 2 h. The reaction was diluted with water (200 mL) and extracted with methyl tert-butyl ether (2×500 mL). The organic phases were dried over sodium sulfate and evaporated under vacuum to provide (4R)-4-(2-chlorothiazol-5-yl)-N-methyl-thiazolidin-2-imine as brown oil [53 g, 98 area % HPLC purity (rt=2.506 min.), m/z=234 amu (M+H⁺)].

Step-7: Preparation of (3R)-3-(2-chlorothiazol-5-yl)-8-methyl-7-oxo-6-phenyl-2,3-dihydrothiazolo[3,2-a]pyrimidin-4-ium-5-olate A 500 mL, three necked flask equipped with magnetic stirrer, reflux condenser and thermo-pocket was charged with (4R)-4-(2-chlorothiazol-5-yl)-N-methyl-thiazolidin-2-imine (53 g, 98% HPLC purity), Toluene (160 mL) and heated to 110° C. under nitrogen atmosphere. Then bis(4-chlorophenyl) 2-phenylpropanedioate (109 g) was added in three portions into the reaction mass kept at 110° C. After stirring at 110° C. for 2 h, HPLC showed >99% conversion. The reaction was cooled between 45 to 50° C. and the precipitated pale yellow colored solid was filtered through sintered funnel, washed with methyl tert-butyl ether (480 mL) and dried under vacuum to provide (3R)-3-(2-chlorothiazol-5-yl)-8-methyl-7-oxo-6-phenyl-2,3-dihydrothiazolo[3,2-a]pyrimidin-4-ium-5-olate [54 g, 98.8 area % HPLC purity (rt=3.86 min.), m/z=378 amu (M+H⁺) & 99% enantiomeric excess by chiral HPLC method 3).

¹H NMR (300 MHz, DMSO-d6): 3.42 (s, 3H), 3.94 (d, J=12 Hz, 1H), 4.25-4.32 (m, 1H), 6.48 (d, J=8.1 Hz, 1H), 7.06-7.11 (m, 1H), 7.21-7.26 (m, 2H), 7.6 (d, J=7.5 Hz, 1H), 7.96 (s, 1H)

Example-2: Preparation of (3R)-3-(2-chlorothiazol-5-yl)-8-methyl-7-oxo-6-phenyl-2,3-dihydrothiazolo[3,2-a]pyrimidin-4-ium-5-olate

Step-1: Preparation of N-[2-chloro-1-(2-chlorothiazol-5-yl)ethylidene]-2-methyl-propane-2-sulfinamide A 0.5 L, three necked flask equipped with Teflon-blade stirrer, reflux condenser and thermo-pocket was charged with 2-chloro-1-(2-chlorothiazol-5-yl)ethanone (60 g, 97 area % purity by HPLC), THF (180 ml), 2-methylpropane-2-sulfinamide (44 g) and Titanium(IV)ethoxide (77 mL) at ambient temperature under nitrogen atmosphere. The resulting mixture was heated to 50° C. and stirred for 2 h. The reaction progress was monitored by HPLC (>95% conversion by HPLC). The reaction was charged with methyl tert-butyl ether (360 ml), cooled to 0 to 10° C., quenched slowly with 1 N aq. HCl solution (540 ml) and stirred for 10 min. The two phases were separated and the organic phase was washed with water (2×300 mL). The organic phase was dried over sodium sulphate, filtered and evaporated to obtain crude residue. The crude product was dissolved in methyl tert-butyl ether (100 ml) at ambient temperature and activated charcoal (1.8 g) and silica (5 g, 60-120 mesh) were added. The slurry was stirred for 0.5 h, filtered through Buchner funnel and washed with methyl tert-butyl ether (0.3 L). The filtrate was evaporated to obtain N-[2-chloro-1-(2-chlorothiazol-5-yl)ethylidene]-2-methyl-propane-2-sulfinamide as pale brown colored oil (88 g, 84% area purity by HPLC method 1).

Step-2: Preparation of N-[(1S)-2-chloro-1-(2-chlorothiazol-5-yl)ethyl]-2-methyl-propane-2-sulfinamide a) Preparation of Rhodium Catalyst—RhCl[(R,R)-TsDPEN]Cp*

The catalyst was prepared as mentioned in step-4 of example 1.

b) Preparation of HCOOH-NEt$_3$ Mixture prepared as described in step-4 of example 1.

c) Preparation of N-[(1S)-2-chloro-1-(2-chlorothiazol-5-yl)ethyl]-2-methyl-propane-2-sulfinamide A 3 L four necked flask equipped with magnetic stirrer, nitrogen inlet and thermo-pocket was charged with dimethylformamide (1.5 L) and degassed with nitrogen for 10 min. Then RhCl[(R,R)-TsDPEN]Cp* (1.87 g) was added under nitrogen atmosphere at 22 to 27° C. To above kept solution, N-[2-chloro-1-(2-chlorothiazol-5-yl)ethylidene]-2-methyl-propane-2-sulfinamide (88 g) dissolved in dimethylformamide (260 ml), and HCOOH-NEt$_3$ (220 mL, in a ratio of 1.1:1) solutions were added simultaneously at 22 to 27° C. over a period of 0.5 h and resulting mixture was stirred at 22-27° C. for 2 h. The HPLC showed >97% conversion. The reaction mixture was quenched with water (1700 ml) and extracted with methyl tert-butyl ether (3×1000 mL). The combined organic phase was evaporated to obtain N-[(1S)-2-chloro-1-(2-chlorothiazol-5-yl)ethyl]-2-methyl-propane-2-sulfinamide (95 g)

Step-3: Preparation of (1S)-2-chloro-1-(2-chlorothiazol-5-yl)ethanamine

A 1 L three necked flask equipped with magnetic stirrer, nitrogen inlet and thermo-pocket was charged with N-[(1S)-2-chloro-1-(2-chlorothiazol-5-yl)ethyl]-2-methyl-propane-2-sulfinamide (95 g) and 1 N HCl in MeOH (285 mL) at ambient temperature and the reaction mixture was stirred at 22-27° C. for 14 h. The reaction progress was monitored by HPLC. The organic volatiles were removed under vacuum and the residue was triturated with methyl tert-butyl ether (3×150 mL) and organic phase containing methyl tert-butyl ether was separated from pale yellow colored oily residue. The pale yellow coloured residue containing (1S)-2-chloro-1-(2-chlorothiazol-5-yl)ethanamine; hydrochloride was neutralized with 1 N aq. NaOH and extracted with MTBE (3×150 ml). The organic phases were dried over sodium sulphate, filtered and evaporated to obtain (1S)-2-chloro-1-(2-chlorothiazol-5-yl)ethanamine as brown coloured residue (35 g; 99.5 area % HPLC purity (rt=2.64 min.), m/z=198 amu (M+H$^+$) & 96.2% ee by chiral HPLC method 1).

Step-4: Preparation of (4R)-4-(2-chlorothiazol-5-yl)-N-methyl-thiazolidin-2-imine A 250 mL, three necked flask equipped with magnetic stirrer, reflux condenser and thermo-pocket was charged with (1S)-2-chloro-1-(2-chlorothiazol-5-yl)ethanamine (35 g, 96.2% ee), ethanol (140 ml), methyl isothiocyanate (19.58 g) and triethylamine (48 ml). The resulting mixture was stirred for 14 h at 22-27° C. The HPLC analysis showed >99% conversion with formation of (4R)-4-(2-chlorothiazol-5-yl)-N-methyl-thiazolidin-2-imine Then organic volatiles were removed under vacuum and sodium hydroxide (17.15 g) and water (140 mL) were added into the reaction flask. The reaction mixture was heated to 100° C. and stirred for 2 h. The reaction was diluted with water (140 mL) and extracted with methyl tert-butyl ether (3×200 mL). The organic phases were dried over sodium sulphate and evaporated under vacuum to provide (4R)-4-(2-chlorothiazol-5-yl)-N-methyl-thiazolidin-2-imine as brown oil [41 g, 96 area % HPLC purity (rt=2.506 min.), m/z=234 amu (M+H$^+$)].

Step-5: Preparation of (3R)-3-(2-chlorothiazol-5-yl)-8-methyl-7-oxo-6-phenyl-2,3-dihydrothiazolo[3,2-a]pyrimidin-4-ium-5-olate A 500 mL, three necked flask equipped with magnetic stirrer, reflux condenser and thermo-pocket was charged with (4R)-4-(2-chlorothiazol-5-yl)-N-methyl-thiazolidin-2-imine (41 g, 96% HPLC purity), Toluene (125 mL) and heated to 110° C. under nitrogen atmosphere. Then bis(4-chlorophenyl) 2-phenylpropanedioate (85 g) was added in three portions into the reaction mass kept at 110° C. After stirring at 110° C. for 2 h, HPLC showed >99% conversion. The reaction was cooled between 45 to 50° C. and the precipitated pale yellow colored solid was filtered through sintered funnel, washed with methyl tert-butyl ether (480 mL) and dried under vacuum to provide (3R)-3-(2-chlorothiazol-5-yl)-8-methyl-7-oxo-6-phenyl-2,3-dihydrothiazolo[3,2-a]pyrimidin-4-ium-5-olate (38 g, 99.3 area % HPLC purity, m/z=378 amu (M+H$^+$) & 99% ee by chiral HPLC method 3).

Example-3: Preparation of (3R)-3-(2-chlorothiazol-5-yl)-8-methyl-7-oxo-6-phenyl-2,3-dihydrothiazolo[3,2-a]pyrimidin-4-ium-5-olate Step-1: Preparation of N-[(1S)-2-chloro-1-(2-chlorothiazol-5-yl)ethyl]-2-methyl-propane-2-sulfinamide a) Preparation of Rhodium Catalyst—RhCl[(R,R)-TsDPEN]Cp*

The catalyst was prepared as mentioned in step-4 of example 1.

b) Preparation of HCOOH-NEt$_3$ Mixture prepared as described in step-4 of example 1.

c) Preparation of N-[(1S)-2-chloro-1-(2-chlorothiazol-5-yl)ethyl]-2-methyl-propane-2-sulfinamide A 20 L reactor, was charged with N-[2-chloro-1-(2-chlorothiazol-5-yl) ethylidene]-2-methyl-propane-2-sulfinamide (1275 g, 2.2 mol, 68% purity by HPLC), dimethyl formamide (2550 ml) & toluene (2550 ml) and degassed with nitrogen for 10 min. Then RhCl[(R,R)-TsDPEN]Cp* (7.0 g, 0.01 mol) was added under nitrogen atmosphere. The resulting mixture was cooled to 0 to 5° C. and the freshly prepared HCOOH-NEt$_3$ (375 mL, in a ratio of 1.1:1) solution was added drop wise over a period of 30 min and stirred between 0° C. to 5° C. for 3 h. The reaction was monitored by HPLC and quenched with water (2550 mL) and extracted with Toluene (2550 mL). The combined organic phase was washed with water (3×3750 ml) and evaporated to obtain N-[(1S)-2-chloro-1-(2-chlorothiazol-5-yl)ethyl]-2-methyl-propane-2-sulfinamide brown colored residue (1150 g, 68% purity by HPLC (rt=4.70 & 4.82 min)).

Step-2: Preparation of (1S)-2-chloro-1-(2-chlorothiazol-5-yl)ethanamine

A 5 L four necked flask equipped with magnetic stirrer, nitrogen inlet and thermo-pocket was charged with N-[(1S)-2-chloro-1-(2-chlorothiazol-5-yl)ethyl]-2-methyl-propane-2-sulfinamide (1150 g) was diluted in MTBE (3210 ml) and HCl gas was purged for 1 h at 25° C. The reaction progress was monitored by HPLC. The precipitated yellow colored hydrochloride salt was filtered, and the residue was washed with MTBE (2×2000 ml) to obtain pale yellow colored solid (500 g). The pale yellow colored solid containing (1S)-2-chloro-1-(2-chlorothiazol-5-yl)ethanamine; hydrochloride was adjusted to pH 8.5 to 9 with 2 N aq. NaOH and extracted with toluene (3×1000 ml). The combined organic phases were washed with water (1 L) and evaporated to obtain (1S)-2-chloro-1-(2-chlorothiazol-5-yl)ethanamine as brown colored residue (370 g; 98% HPLC purity (rt=2.64 min.), m/z=198 amu (M+H$^+$) & 93% ee by chiral HPLC method 1).

Step-3: Preparation of (4R)-4-(2-chlorothiazol-5-yl)-N-methyl-thiazolidin-2-imine A 2 L three necked flask equipped with magnetic stirrer, reflux condenser and thermo-pocket was charged with (1S)-2-chloro-1-(2-chlorothiazol-5-yl)ethanamine (165 g, 0.83 mol, with 93% ee), Methanol (400 ml), Methyl isothiocyanate (91.86 g, 1.25 mol) and triethylamine (225 ml, 1.67 mol) at ambient temperature. The resulting mixture was stirred for 14 h at 22-27° C. The HPLC analysis showed >99% conversion with formation of (4R)-4-(2-chlorothiazol-5-yl)-N-methyl-thiazolidin-2-imine. Then sodium hydroxide (67 g, 1.67 mol) and water (660 mL) were added into the reaction flask. The reaction mixture was heated to 65° C. and stirred for 2 h. The reaction mixture was extracted with Toluene (3×660 mL). The combined organic phases were dried over sodium sulfate and evaporated under vacuum to provide (4R)-4-(2-chlorothiazol-5-yl)-N-methyl-thiazolidin-2-imine as brown oil (198 g, 94 area % HPLC purity), m/z=234 amu (M+H+)).

Step-4: Preparation of (3R)-3-(2-chlorothiazol-5-yl)-8-methyl-7-oxo-6-phenyl-2,3-dihydrothiazolo[3,2-a]pyrimidin-4-ium-5-olate A 20 L reactor, was charged with (4R)-4-(2-chlorothiazol-5-yl)-N-methyl-thiazolidin-2-imine (2070 g, 98% HPLC purity), toluene (4140 mL) and heated to 80° C. under nitrogen atmosphere. Then bis(4-chlorophenyl) 2-phenyl-propanedioate (3553 g, 8.8 mol) was dissolved in toluene (4140 ml) at 45° C. and added drop wise into the reaction mass kept at 80° C. After stirring at 100° C. for 1 h, HPLC showed >99% conversion. The reaction was cooled below 40° C. and the precipitated pale yellow colored solid was filtered & washed with Toluene (3×2070 ml) to provide (3R)-3-(2-chlorothiazol-5-yl)-8-methyl-7-oxo-6-phenyl-2,3-dihydrothiazolo[3,2-a]pyrimidin-4-ium-5-olate as 1st lot (1660 g, 99 area % HPLC purity & 100% enantiomeric excess) The combined mother liquor was transferred to 20 L reactor, acetone (6210 ml) was added and stirred at 22-27° C. for 1 h. The precipitated pale yellow colored solid was filtered and washed with toluene (2070 ml×3) to obtain (3R)-3-(2-chlorothiazol-5-yl)-8-methyl-7-oxo-6-phenyl-2,3-dihydrothiazolo[3,2-a]pyrimidin-4-ium-5-olate as 2$^{nd}$ lot (718 g, 99 area % HPLC purity & 100% enantiomeric excess by chiral HPLC method 3).

Example-4: Preparation of Preparation of (1S)-2-chloro-1-(2-chlorothiazol-5-yl)ethanamine Step-1: Preparation of N-[(1S)-2-chloro-1-(2-chlorothiazol-5-yl)ethyl]-2-methyl-propane-2-sulfinamide a) Preparation of HCOOH-NEt$_3$ Mixture prepared as described in step-4 of example 1.

b) Preparation of N-[(1S)-2-chloro-1-(2-chlorothiazol-5-yl)ethyl]-2-methyl-propane-2-sulfinamide A 1 L 3 neck round bottom flask, was charged with N-[2-chloro-1-(2-chlorothiazol-5-yl) ethylidene]-2-methyl-propane-2-sulfinamide (50 g, 85% HPLC purity), dimethylformamide (100 ml), toluene (100 ml) and degassed with nitrogen for 10 min. Then pentamethylcyclopentadienyl rhodium chloride dimer (150 mg) & (1R,2R)—N-p-toluenesulfonyl-1,2-diphenylethylenediamine (170 mg) were added under nitrogen atmosphere at ambient temperature. The resulting mixture was cooled to 0 to 5° C. & freshly prepared HCOOH-NEt$_3$ (15 mL, in a ratio of 1.1:1) was added & stirred for 2 h. The reaction was monitored by HPLC and quenched with water (100 mL) and extracted with Toluene (200 mL). The combined organic phase was washed with water (3×20 ml) and evaporated to obtain N-[(1S)-2-chloro- 1-(2-chlorothiazol-5-yl)ethyl]-2-methyl-propane-2-sulfinamide brown colored residue (49 g, 88% purity by HPLC).

Step-2: Preparation of (1S)-2-chloro-1-(2-chlorothiazol-5-yl)ethanamine

A 5 L four necked flask equipped with magnetic stirrer, nitrogen inlet and thermo-pocket was charged with N-[(1S)-2-chloro-1-(2-chlorothiazol-5-yl)ethyl]-2-methyl-propane-2-sulfinamide (49 g) was diluted in MTBE (147 ml) and HCl gas was purged for 15 min at 25° C. to 30° C. The reaction progress was monitored by HPLC. The precipitated yellow colored hydrochloride salt was filtered, and the residue was washed with MTBE (2×100 ml) to obtain pale yellow colored solid (35 g). The pale yellow colored solid containing (1S)-2-chloro-1-(2-chlorothiazol-5-yl)ethanamine; hydrochloride was adjusted to pH 8.5 with 2 N aq. NaOH and extracted with Toluene (3×80 ml). The combined organic phases were washed with water (100 ml) and evaporated to obtain (1S)-2-chloro-1-(2-chlorothiazol-5-yl)ethanamine as brown colored residue (30 g; m/z=198 amu (M+H+), 98.5% HPLC purity & 99% ee by chiral HPLC method 1).

Example-5: Preparation of (3R)-3-(2-chlorothiazol-5-yl)-6-(3,5-dichlorophenyl)-8-methyl-7-oxo-2,3-dihydrothiazolo[3,2-a]pyrimidin-4-ium-5-olate A process analogous to the process described in step-4 of example 3 was followed. The reaction was conducted using (4R)-4-(2-chlorothiazol-5-yl)-N-methyl-thiazolidin-2-imine (1 g, 96% HPLC purity), toluene (3 mL) and bis(4-chlorophenyl) 2-(3,5-dichlorophenyl)propanedioate (2.8 g) to obtain (3R)-3-(2-chlorothiazol-5-yl)-6-(3,5-dichlorophenyl)-8-methyl-7-oxo-2,3-dihydrothiazolo[3,2-a]pyrimidin-4-ium-5-olate (1.1 g & 94% enantiomeric excess by chiral HPLC method 3 (rt=5.01 min), m/z=448 amu (M+H+)).

Example-6: Preparation of (3R)-3-(2-chlorothiazol-5-yl)-6-(4-methoxyphenyl)-8-methyl-7-oxo-2,3-dihydrothiazolo[3,2-a]pyrimidin-4-ium-5-olate A process analogous to the process described in step-4 of example 3 was followed. The reaction was conducted using (4R)-4-(2-chlorothiazol-5-yl)-N-methyl-thiazolidin-2-imine (1 g, 96% HPLC purity), toluene (3 mL) and bis(4-chlorophenyl) 2-(4-methoxyphenyl)propanedioate (2.6 g) to obtain (3R)-3-(2-chlorothiazol-5-yl)-6-(4-methoxyphenyl)-8-methyl-7-oxo-2,3-dihydrothiazolo[3,2-a]pyrimidin-4-ium-5-olate (1.1 g & 95% enantiomeric excess by chiral HPLC method 3 (rt=3.85 min), m/z=408 amu (M+H+)).

Example-7: Preparation of (3R)-3-(2-chlorothiazol-5-yl)-8-methyl-7-oxo-6-[3-(trifluoromethyl)phenyl]-2,3-dihydrothiazolo[3,2-a]pyrimidin-4-ium-5-olate A process analogous to the process described in step-4 of example 3 was followed. The reaction was conducted using (4R)-4-(2-chlorothiazol-5-yl)-N-methyl-thiazolidin-2-imine (1 g, 96% HPLC purity), toluene (3 mL) and bis(4-chlorophenyl) 2-(3-(trifluoromethyl)phenyl)propanedioate (2.7 g) to obtain (3R)-3-(2-chlorothiazol-5-yl)-8-methyl-7-oxo-6-[3-(trifluoromethyl)phenyl]-2,3-dihydrothiazolo[3,2-a]pyrimidin-4-ium-5-olate (1.05 g & 97% enantiomeric excess by chiral HPLC method 3 (rt=4.66 min), m/z=446 amu (M+H+)).

The invention claimed is:
1. A process for preparing a compound of formula VI

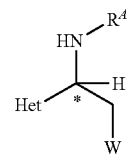

VI wherein
C* is an asymmetric carbon atom of S or R-configuration;
Het is selected from the group consisting of D-1, D-2, and D-3:

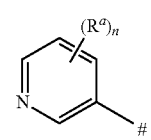

D-1

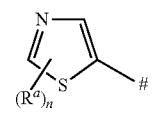

D-2

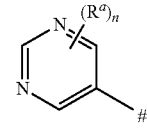

D-3 wherein
$R^a$ is each independently halogen, $C_1$-$C_4$-haloalkyl, $C_1$-$C_4$-alkoxy, $C_1$-$C_4$-alkylthio, or phenyl;
n is 0, 1 or 2, and
# denotes the bond in formula X;
$R^A$ is $S(=O)_o R^x$, $P(=O)(R^x)_2$, $C_1$-$C_4$-alkoxy, or —$CH_2$-phenyl, wherein phenyl is unsubstituted or substituted with halogen, methoxy, or nitro; wherein
$R^x$ is $C_1$-$C_6$ alkyl or aryl which is unsubstituted or substituted with halogen; and
o is 1 or 2; and
W is halogen, hydroxy, O-p-toluenesulphonyl, O-methanesulphonyl, or O-trifluoromethanesulphonyl;
comprising the step of:
(A) hydrogenation of a compound of formula V,

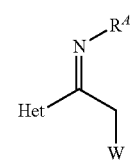

V in the presence of a hydrogenation catalyst MXLn(η-arene)$_m$,
wherein
M is a transition metal from group VIII to group XII of the periodic table;

X is an anion;
m is 0 or 1;
Ln is Ln1 or Ln2,
wherein
Ln1 is a chiral ligand of the formula Ln1

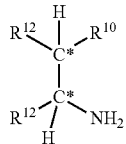

wherein
C* is an asymmetric carbon atom of S or R-configuration;
$R^{10}$ is OH or NH—$SO_2$—$R^{11}$; wherein
  $R^{11}$ is aryl unsubstituted or substituted independently of each other with halogen, $C_1$-$C_{10}$-alkyl, $C_1$-$C_4$-alkoxy, $C_3$-$C_6$-cycloalkyl, $SO_3H$, or $SO_3Na$
  or
  $R^{11}$ is $C_1$-$C_{10}$-perfluoroalkyl, or $R^{13}R^{14}N$ wherein $R^{13}$ and $R^{14}$ independently represent $C_1$-$C_{10}$-alkyl unsubstituted or substituted with $C_6$-$C_{10}$-aryl, or $R^{13}$ and $R^{14}$ each independently represents a $C_6$-$C_{10}$-cycloalkyl;
$R^{12}$ independently represents $C_6$-$C_{10}$-aryl ring or $C_6$—$C_{10}$-cycloalkyl ring, wherein the ring is aryl unsubstituted or substituted independently of each other with halogen, $C_1$-$C_{10}$-alkyl, $C_1$-$C_4$-alkoxy, $C_3$-$C_6$-cycloalkyl, $SO_3H$, or $SO_3Na$, or both $R^{12}$ are linked together to form a 3- to 6-membered carbocyclic ring or a 5- to 10-membered partially unsaturated carbocyclic ring;
Ln2 is a chiral phosphorous ligand;
and a hydrogen source selected from the group consisting of a) hydrogen, b) mixture of $N(R)_3$ wherein R is H or $C_1$-$C_6$-alkyl, and HCOOH, c) HCOONa or HCOOK, d) mixture of $C_1$-$C_8$-alcohol and t-BuOK, t-BuONa, or t-BuOLi, and e) combination of two or more from a) to d);
to obtain a compound of formula VI,

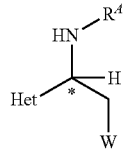

wherein C* is an asymmetric carbon atom of S or R-configuration.

2. A process for preparing a compound of formula VII,

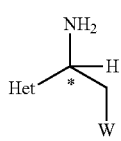

wherein
C* is an asymmetric carbon atom of S or R-configuration;
Het is selected from the group consisting of D-1, D-2, and D-3:

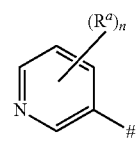

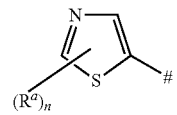

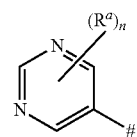

wherein
$R^a$ is each independently halogen, $C_1$-$C_4$-haloalkyl, $C_1$-$C_4$-alkoxy, $C_1$-$C_4$-alkylthio, or phenyl;
n is 0, 1 or 2, and
# denotes the bond in formula X; and
W is halogen, hydroxy, O-p-toluenesulphonyl, O-methanesulphonyl, or O-trifluoromethanesulphonyl;
comprising the step of hydrolyzing the compound of the formula VI,

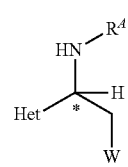

wherein
$R^A$ is $S(=O)_oR^x$, $P(=O)(R^x)_2$, $C_1$-$C_4$-alkoxy, or —$CH_2$-phenyl, wherein phenyl is unsubstituted or substituted with halogen, methoxy, or nitro; wherein
  $R^x$ is $C_1$-$C_6$ alkyl or aryl which is unsubstituted or substituted with halogen; and
  o is 1 or 2;
in the presence of an acid or a base,
to obtain a compound of formula VII,

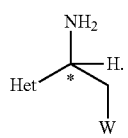

3. A process of preparing an optically active pyrimidinium compound of formula X,

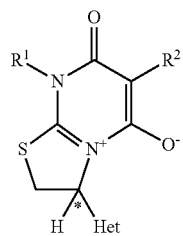

X wherein

C* is an asymmetric carbon atom of S or R-configuration;

$R^1$ is $C_1$-$C_4$-alkyl, $C_3$-$C_6$-cycloalkyl, $C_2$-$C_4$-alkenyl or —$CH_2$-phenyl, which groups are unsubstituted or substituted with halogen or $C_1$-$C_4$-alkyl;

$R^2$ is a 5- or 6-membered saturated, partially unsaturated or aromatic carbo- or heterocyclic ring, wherein the ring is unsubstituted or substituted with Rea;

Het is selected from the group consisting of D-1, D-2, and D-3:

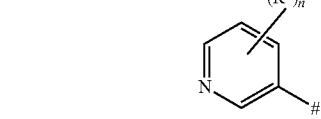

D-1

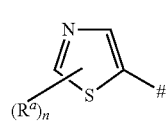

D-2

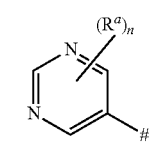

D-3 wherein $R^a$ is each independently halogen, $C_1$-$C_4$-haloalkyl, $C_1$-$C_4$-alkoxy, $C_1$-$C_4$-alkylthio, or phenyl;

n is 0, 1 or 2, and # denotes the bond in formula X;

$R^{2a}$ is halogen, $C_1$-$C_6$-haloalkyl, $C_1$-$C_6$-haloalkoxy, OW, C(=O)$OR^c$, C(=O)$NR^bR^c$, phenyl, or pyridyl, which groups are unsubstituted or substituted with halogen, $C_1$-$C_6$-haloalkyl or $C_1$-$C_6$-haloalkoxy;

$R^b$ is hydrogen, $C_1$-$C_6$-alkyl, $C_1$-$C_6$-haloalkyl, $C_1$-$C_6$-alkoxy, or $C_1$-$C_6$-haloalkoxy;

$R^c$ is hydrogen, $C_1$-$C_4$-alkyl, $C_1$-$C_4$-haloalkyl, or $C_1$-$C_6$-cycloalkyl;

wherein two geminally bound groups $R^cR^b$ together with the atom to which they are bound may form a 3- to 7-membered saturated, partially unsaturated or aromatic heterocyclic ring;

comprising the steps of reacting the compound of formula VII

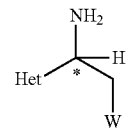

VII wherein

W is halogen, hydroxy, O-p-toluenesulphonyl, O-methanesulphonyl, or O-trifluoromethanesulphonyl;

with $R^1$NCS, wherein $R^1$ is $C_1$-$C_4$-alkyl, $C_3$-$C_6$-cycloalkyl, $C_2$-$C_4$-alkenyl or —$CH_2$-phenyl, which groups are unsubstituted or substituted with halogen or $C_1$-$C_4$-alkyl; in the presence of a base to obtain a compound of formula VIII,

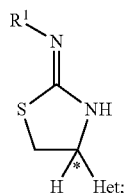

VIII and reacting the compound of formula VIII with a compound of formula IX

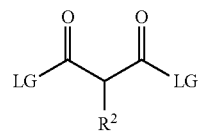

IX wherein,

LG is a leaving group selected from the group consisting of halogen, $OR^u$ and $SR^u$; wherein $R^u$ is $C_1$-$C_6$-alkyl or aryl, which is unsubstituted or substituted with halogen;

to obtain the compound of formula X.

4. The process of claim 1, wherein in step (A) the chiral phosphorous ligand Ln2 is selected from the ligands listed in Table-A below or selected from their corresponding enantiomers,

TABLE-A

| Sr. No. | Structure | Name |
|---|---|---|
| 1. | 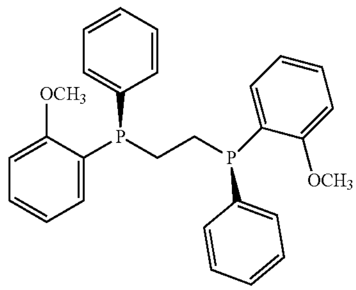 [SMILES: COc1ccccc1[P@](CC[P@](c1ccccc1)c1ccccc1OC)c1ccccc1] | (R,R)-DIPAMP |
| 2. | 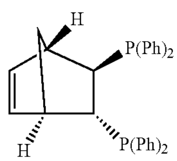 | (R,R)-NORPHOS |
| 3. | 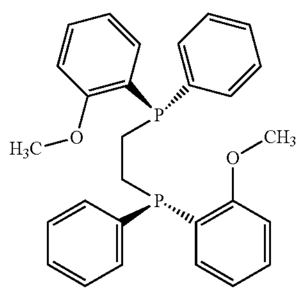 | (S,S)-DIPAMP |
| 4. | 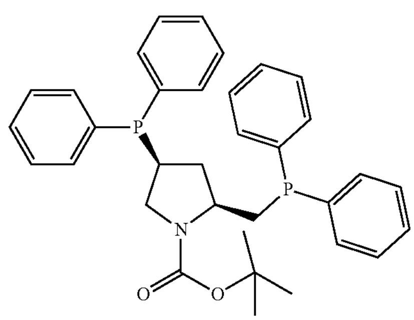 [SMILES: CC(C)(C)OC(=O)N1C[C@@H](P(c2ccccc2)c2ccccc2)C[C@H]1CP(c1ccccc1)c1ccccc1] | (S,S)-BPPM |
| 5 | 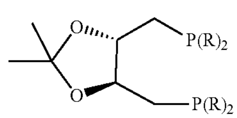 | (S,S)-DIOP: R = Ph (S,S)-Cy-DIOP: R = Cy (S,S)-MOD-DIOP: R = 3,5-$(CH_3)_2$-4-$(CH_3O)C_6H_2$ |
| 6 | 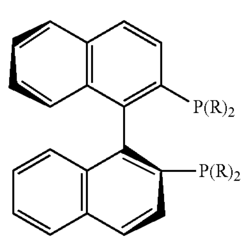 | (S)-BINAP: R = Ph (S)-TolBINAP: R = 4-$CH_3C_6H_4$ (S)-XylBINAP: R = 3,5-$(CH_3)2$-$C_6H_3$ |

TABLE-A-continued

| Sr. No. | Structure | Name |
|---|---|---|
| 7 | [structure: biphenyl with PR¹ and P(R)₂ groups at 2,2' and 6,6' positions] | (S)-BICHEP: R = Cy; R¹ = CH₃ (S)-BIPHEMP: R = Ph; R¹ = CH₃ (S)-BICHEP: R = Ph; R¹ = OCH₃ |
| 8 | [structure: pyrrolidine with PCy₂ and CH₂PPh₂ substituents, N-COX] | (S,S)BCPM: X = OC(CH₃)₃ (S,S)-MCCPM: X = NHCH₃ |
| 9 | [structure: 2,4-pentanediyl bis(diphenylphosphine)] | (S,S)-BDPP |
| 10 | [structure: N-benzyl pyrrolidine with two PPh₂ groups at 3,4 positions] | (S,S)-PYRPHOS |
| 11 | [structure: 1,2-bis(phospholanyl)ethane with R groups] | (S,S)-Me-BPE: R = CH₃ (S,S)-Et-BPE: R = C₂H₅ (S,S)-iPr-BPE: R = iso-(CH₃)₂ |
| 12 | [structure: 1,2-bis(phospholanyl)benzene with R groups] | (S,S)-Me-DuPhos: R = CH₃ (S,S)-Et-DuPhos: R = C₂H₅ (S,S)-iPr-DuPhos: R = CH(CH₃)₃ |

TABLE-A-continued

| Sr. No. | Structure | Name |
|---|---|---|
| 13 | (structure) | (S)-o-Ph-HexaMeO-BIPHEP |
| 14 | (structure) | (S,S)BINAPHANE |
| 15 | (structure) | (R,R)-BCIP |
| 16 | (structure) | (R,S,S,R)-DIOP* |
| 17 | (structure) | (R)-(S)-Josiphos: R = Cy, R' = Ph<br>(R)-(S)-PPF-t-Bu₂: R = t-Bu, R' = Ph<br>(R)-(S)-Xyliphos: R = 3,5-Me₂-C₆H₃, R' = Ph<br>(R)-(S)-Cy₂PF-PCy₂: R = R' = Cy |
| 18 | (structure) | (S,S)-FerroPHOS |

TABLE-A-continued

| Sr. No. | Structure | Name |
|---|---|---|
| 19 | 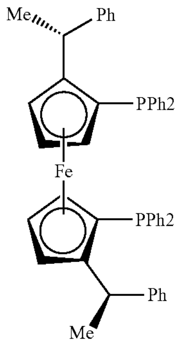 | FERRIPHOS |
| 20 | 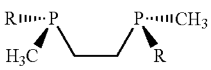 | (S,S)-BisP*<br>(S,S)-tBu-BisP*: R = tBu<br><br>(S,S)-Ad-BisP*: R = 1-adamantyl<br>(S,S)-Cy-BisP*: R = Cy |
| 21 | 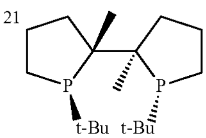 | (S,S,R,R)-TangPhos |
| 222 | 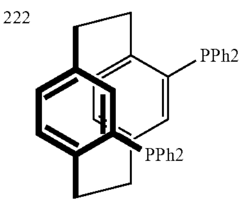 | (S)-[2,2]-PHENOPHOS |
| 23 | 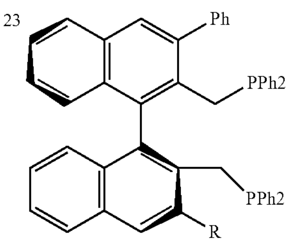 | (S)-Ph-o-NAPHOS |
| 24 | 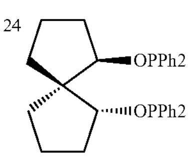 | (R)-spirOP |
| 25 | 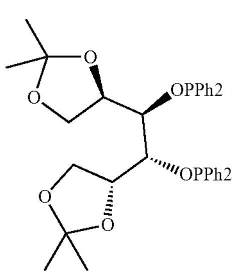 | DIMOP |

TABLE-A-continued

| Sr. No. | Structure | Name |
|---|---|---|
| 26 | (naphthyl structure with OPPh2 groups and R substituents) | BINAPO: R = H<br>(S)-Ph-o-BINAPO: R = Ph |
| 27 | (pyrrolidinone structure with P(R)2 groups) | (S)-Cy,Cy-oxoProNOP: R = Cy<br>(S)-Cp,Cp-oxoProNOP: R = Cp |
| 28 | (structure with Ph, PPh2, N-Me groups) | (1R,2S)-DPAMPP |
| 29 | (binaphthyl with NHPAr2 groups) | (R)-BDPAB: Ar = Ph<br>(R)-Xyl-BDP: Ar = 3,5-Me$_2$C$_6$H$_3$ |
| 30 | (octahydro-binaphthyl with NHPPh2 groups) | (R)-H$_8$-BDPAB. | wherein Cy = cyclohexyl and Ph = phenyl.

5. The process of claim 1, wherein η-arene is selected from the group consisting of benzene, p-cymene, mesitylene, 1,3,5-triethylbenzene, hexamethylbenzene, anisole, 1,5-cyclooctadiene, cyclopentadienyl (Cp), norbornadiene, and pentamethylcyclopentadienyl (Cp*).

6. The process of claim 1, wherein MXLn(η-arene), is MXLn1(η-arene), and wherein $R^{10}$ is NH—SO$_2$—$R^{11}$; and $R^{12}$ and $R^{11}$ independently are phenyl which are unsubstituted or substituted with 1 or 2 substituents selected from the group consisting of halogen, C$_1$-C$_4$-alkyl, C$_1$-C$_4$-alkoxy, C$_3$-C$_6$-cycloalkyl, SO$_3$H, and SO$_3$Na.

7. The process of claim 1, wherein MXLn(η-arene), is MXLn1(η-arene), and wherein X is halide; $R^{12}$ independently is phenyl, 2-methylphenyl, 3-methylphenyl, 4-methylphenyl or 4-methoxyphenyl; $R^{10}$ is NH—SO$_2$—$R^{11}$ and —SO$_2$—$R^{11}$ is p-toluenesulphonyl, methanesulphonyl, 4-benzenesulfonyl, or pentafluorophenyl-sulfonyl.

8. The process of claim 1, wherein m is 1 and MXLn(η-arene), is of the formula MXLnCp*, wherein M is rhodium, ruthenium, iridium, palladium, iron, platinum, or nickel.

9. The process of claim 1, wherein M is rhodium, ruthenium, or iridium.

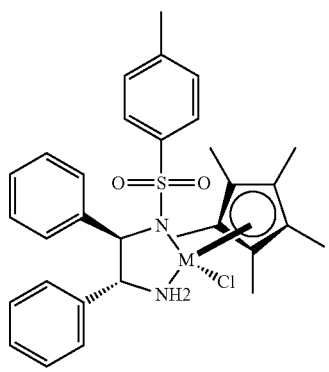

MXLnCp*

10. The process of claim 2, wherein the acid in step (B) is selected from the group consisting of hydrochloric acid, sulphuric acid, phosphoric acid, polyphosphoric acid, hydroiodic acid, $C_1$-$C_8$-alkyl-$(COOH)_y$, $C_1$-$C_8$-haloalkyl-$(COOH)y$, $CH_3SO_3H$, citric acid, oxalic acid, p-toluenesulphonic acid, and mixtures of two or more thereof; wherein y is 1 or 2.

11. The process of claim 1, wherein $R^1$ is $C_1$-$C_4$-alkyl, $C_3$-$C_6$-cycloalkyl, or $C_2$-$C_4$-alkenyl, which is unsubstituted, or substituted with halogen.

12. The process of claim 1, wherein
    $R^2$ is phenyl, pyridinyl or thiophenyl, which is unsubstituted or substituted with $R^{2a}$.

13. The process of claim 1, wherein Het is D-2 wherein n is 0 and $R^a$ is halogen.

14. A compound of formula V,

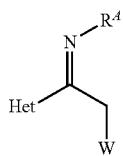

wherein $R^A$ is $S(=O)_oR^x$, $P(=O)(R^x)_2$, $C_1$-$C_4$-alkoxy, or —$CH_2$-phenyl, wherein phenyl is unsubstituted or substituted with halogen, methoxy, or nitro;

W is halogen, hydroxy, O-p-toluenesulphonyl, O-methanesulphonyl, or O-trifluoromethanesulphonyl; and Het is selected from the group consisting of D-1, D-2, and D-3:

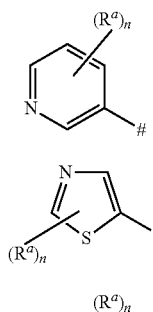

wherein $R^a$ is each independently halogen, $C_1$-$C_4$-haloalkyl, $C_1$-$C_4$-alkoxy, $C_1$-$C_4$-alkylthio, or phenyl;

n is 0, 1 or 2, and # denotes the bond in formula V.

15. An optically active compound of formula VI

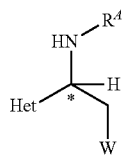

wherein

C* is an asymmetric carbon atom of S or R-configuration;

$R^A$ is $S(=O)_oR^x$, $P(=O)(R^x)_2$, $C_1$-$C_4$-alkoxy, or —$CH_2$-phenyl, wherein phenyl is unsubstituted or substituted with halogen, methoxy, or nitro;

W is halogen, hydroxy, O-p-toluenesulphonyl, O-methanesulphonyl, or O-trifluoromethanesulphonyl; and Het is selected from the group consisting of D-1, D-2, and D-3:

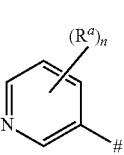

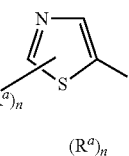

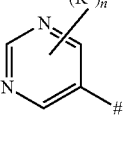

wherein $R^a$ is each independently halogen, $C_1$-$C_4$-haloalkyl, $C_1$-$C_4$-alkoxy, $C_1$-$C_4$-alkylthio, or phenyl;

n is 0, 1 or 2, and # denotes the bond in formula VI.

16. An optically active compound of formula VII

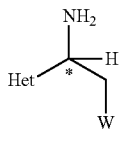

wherein

C* is an asymmetric carbon atom of S or R-configuration;

W is halogen, hydroxy, O-p-toluenesulphonyl, O-methanesulphonyl, or O-trifluoromethanesulphonyl; and Het is D-2 or D-3:

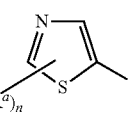

-continued

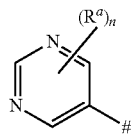
D-3 wherein
$R^a$ is each independently halogen, $C_1$-$C_4$-haloalkyl, $C_1$-$C_4$-alkoxy, $C_1$-$C_4$-alkylthio, or phenyl;
n is 0, 1 or 2, and
# denotes the bond in formula VII.

17. An optically active compound of formula VIII

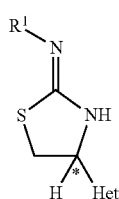
VIII wherein
C* is an asymmetric carbon atom of S or R-configuration;
Het is selected from the group consisting of D-1, D-2, and D-3:

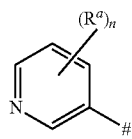
D-1

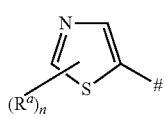
D-2

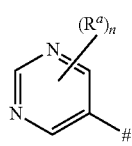
D-3 wherein
$R^a$ is each independently halogen, $C_1$-$C_4$-haloalkyl, $C_1$-$C_4$-alkoxy, $C_1$-$C_4$-alkylthio, or phenyl;
n is 0, 1 or 2, and
# denotes the bond in formula VIII; and
$R^1$ is $C_1$-$C_4$-alkyl, $C_3$-$C_6$-cycloalkyl, $C_2$-$C_4$-alkenyl or —$CH_2$-phenyl, which groups are unsubstituted or substituted with halogen or $C_1$-$C_4$-alkyl.

18. An optically active compound of formula VIII

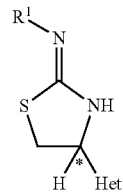
VIII wherein
C* is an asymmetric carbon atom of S or R-configuration;
Het is selected from the group consisting of D-1, D-2, and D-3:

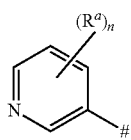
D-1

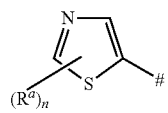
D-2

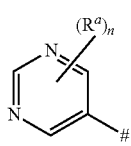
D-3 wherein
$R^a$ is each independently halogen, $C_1$-$C_4$-haloalkyl, $C_1$-$C_4$-alkoxy, $C_1$-$C_4$-alkylthio, or phenyl;
n is 0, 1 or 2, and
# denotes the bond in formula VIII; and
$R^1$ is $C_1$-$C_4$-alkyl, $C_3$-$C_6$-cycloalkyl, or $C_2$-$C_4$-alkenyl, which is unsubstituted, or substituted with halogen.

19. A process for preparing an optically active pyrimidinium compound of formula X

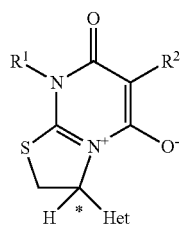
X wherein
C* is an asymmetric carbon atom of S or R-configuration;
$R^1$ is $C_1$-$C_4$-alkyl, $C_3$-$C_6$-cycloalkyl, $C_2$-$C_4$-alkenyl or —$CH_2$-phenyl, which groups are unsubstituted or substituted with halogen or $C_1$-$C_4$-alkyl;
$R^2$ is a 5- or 6-membered saturated, partially unsaturated or aromatic carbo- or heterocyclic ring, wherein the ring is unsubstituted or substituted with Rea;
Het is selected from the group consisting of D-1, D-2, and D-2:

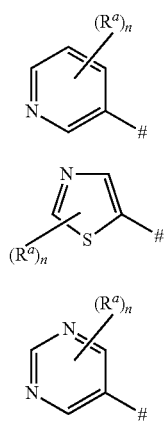

D-1

D-2

D-3 wherein
R$^a$ is each independently halogen, $C_1$-$C_4$-haloalkyl, $C_1$-$C_4$-alkoxy, $C_1$-$C_4$-alkylthio, or phenyl;
n is 0, 1 or 2, and
# denotes the bond in formula X;
R$^{2a}$ is halogen, $C_1$-$C_6$-haloalkyl, $C_1$-$C_6$-haloalkoxy, OR$^c$, C(=O)OR$^c$, C(=O)NR$^b$R$^c$, phenyl, or pyridyl, which groups are unsubstituted or substituted with halogen, $C_1$-$C_6$-haloalkyl or $C_1$-$C_6$-haloalkoxy;
R$^b$ is hydrogen, $C_1$-$C_6$-alkyl, $C_1$-$C_6$-haloalkyl, $C_1$-$C_6$-alkoxy, or $C_1$-$C_6$-haloalkoxy;
R$^c$ is hydrogen, $C_1$-$C_4$-alkyl, $C_1$-$C_4$-haloalkyl, or 01-$O_6$-cycloalkyl;
wherein two geminally bound groups R$_c$R$^b$ together with the atom to which they are bound may form a 3- to 7-membered saturated, partially unsaturated or aromatic heterocyclic ring;
comprising the steps of:
(A) hydrogenation of a compound of formula V,

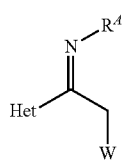

V wherein
R$^A$ is S(=O)$_o$R$^x$, P(=O)(R$^x$)$_2$, $C_1$-$C_4$-alkoxy, or —CH$_2$-phenyl, wherein phenyl is unsubstituted or substituted with halogen, methoxy, or nitro; and
R$^x$ is $C_1$-$C_6$ alkyl or aryl which is unsubstituted or substituted with halogen; and
o is 1 or 2;
W is halogen, hydroxy, O-p-toluenesulphonyl, O-methanesulphonyl, or O-trifluoromethanesulphonyl;
in the presence of a hydrogenation catalyst MXLn(η-arene)$_m$,
wherein
M is a transition metal from group VIII to group XII of the periodic table;
X is an anion;
m is 0 or 1;
Ln is Ln1 or Ln2, wherein
Ln1 is a chiral ligand of the formula Ln1

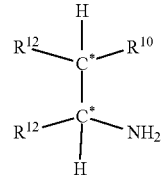

Ln1 wherein
C* is an asymmetric carbon atom of S or R-configuration;
R$^{10}$ is OH or NH—SO$_2$—R$^{11}$; wherein
R$^{11}$ is aryl unsubstituted or substituted independently of each other with halogen, $C_1$-$C_{10}$-alkyl, $C_1$-$C_4$-alkoxy, $O_3$-$O_6$-cycloalkyl, SO$_3$H, or SO$_3$Na
or
R$^{11}$ is $C_1$-$C_{10}$-perfluoroalkyl, or R$^{13}$R$^{14}$N wherein R$^{13}$ and R$^{14}$ independently represent $C_1$-$C_{10}$-alkyl unsubstituted or substituted with $C_6$-$C_{10}$-aryl, or R$^{13}$ and R$^{14}$ each independently represents a $C_6$-$C_{10}$-cycloalkyl;
R$^{12}$ independently represents $C_6$-$C_{10}$-aryl ring or $C_6$-$C_{10}$-cycloalkyl ring, wherein the ring is aryl unsubstituted or substituted independently of each other with halogen, $C_1$-$C_{10}$-alkyl, $C_1$-$C_4$-alkoxy, $C_3$-$C_6$-cycloalkyl, SO$_3$H, or SO$_3$Na, or both R$^{12}$ are linked together to form a 3- to 6-membered carbocyclic ring or a 5- to 10-membered partially unsaturated carbocyclic ring;
Ln2 is a chiral phosphorous ligand;
and a hydrogen source selected from the group consisting of a) hydrogen, b) mixture of N(R)$_3$ wherein R is H or 01-$O_6$-alkyl, and HCOOH, c) HCOONa or HCOOK, d) mixture of $C_1$-$C_8$-alcohol and t-BuOK, t-BuONa, or t-BuOLi, and e) combination of two or more from a) to d);
to obtain a compound of formula VI,

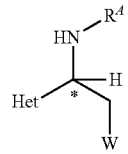

VI wherein C* is an asymmetric carbon atom of S or R-configuration;
(B) hydrolyzing the compound of the formula VI in the presence of an acid or a base, to obtain a compound of formula VII,

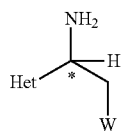

VII (C) reacting the compound of formula VII with R$^1$NCS, wherein R$^1$ is $C_1$-$C_4$-alkyl, $C_3$-$C_6$-cycloalkyl, $C_2$-$C_4$-alkenyl or —CH$_2$-phenyl, which groups are unsubstituted or substituted with halogen or $C_1$-$C_4$-alkyl; in the presence of a base to obtain a compound of formula VIII,

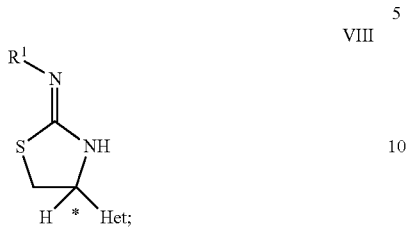

and (D) reacting the compound of formula VIII with a compound of formula IX

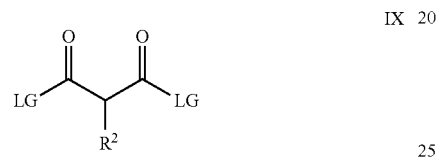

wherein,

LG is a leaving group selected from the group consisting of halogen, $OR^u$ and $SR^u$; wherein $R^u$ is $C_1$-$C_6$-alkyl or aryl, which is unsubstituted or substituted with halogen;

to obtain the compound of formula X.

* * * * *